(12) United States Patent
Korkuch et al.

(10) Patent No.: US 11,224,724 B2
(45) Date of Patent: Jan. 18, 2022

(54) CATHETER INSERTION DEVICE

(71) Applicant: TELEFLEX MEDICAL INCORPORATED, Research Triangle Park, NC (US)

(72) Inventors: Chris Korkuch, Chester Springs, PA (US); Jeffrey P. Kuehn, Schuylkill Haven, PA (US); Drew Pieprzyk, Reading, PA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 355 days.

(21) Appl. No.: 16/247,249

(22) Filed: Jan. 14, 2019

(65) Prior Publication Data

US 2019/0143082 A1    May 16, 2019

Related U.S. Application Data

(60) Division of application No. 14/306,698, filed on Jun. 17, 2014, now Pat. No. 10,357,635, which is a (Continued)

(51) Int. Cl.
*A61M 25/06* (2006.01)
*A61M 25/01* (2006.01)

(52) U.S. Cl.
CPC ..... *A61M 25/0606* (2013.01); *A61M 25/0113* (2013.01); *A61M 25/0618* (2013.01)

(58) Field of Classification Search
CPC .......... A61M 25/0113; A61M 25/0606; A61M 25/0618
See application file for complete search history.

(56) References Cited

U.S. PATENT DOCUMENTS 4,160,383 A    7/1979 Rauschenberger
4,616,648 A   10/1986 Simpson
(Continued)

FOREIGN PATENT DOCUMENTS

CN    1178707 A    4/1998
CN  101242868 A    8/2008
(Continued)

OTHER PUBLICATIONS

International Search Report for corresponding International Application No. PCT/US2014/042671 dated Oct. 28, 2014 (1 page).
(Continued)

*Primary Examiner* — Brandy S Lee
(74) *Attorney, Agent, or Firm* — BakerHostetler

(57) ABSTRACT

A catheter insertion device that allows for single-handed insertion of the catheter within the vasculature of the patient is disclosed. The catheter insertion device includes an insertion group and a catheter group. The insertion group includes a handle, a needle cannula partially within the handle, and a needle support connected to the handle. The catheter group includes an elongated catheter and a catheter hub connected to the proximal end of the elongated catheter. The needle support includes two parallel features separated by a distance greater than an outer diameter of the elongated catheter to stabilize the needle cannula during insertion of the needle cannula into a patient. The needle cannula includes a cantilever portion extending from the handle. The needle support stabilizes the needle cannula during insertion of the needle cannula into a patient.

19 Claims, 33 Drawing Sheets

Related U.S. Application Data continuation-in-part of application No. 14/205,307, filed on Mar. 11, 2014, now Pat. No. 9,717,886.

(60) Provisional application No. 61/778,302, filed on Mar. 12, 2013, provisional application No. 61/865,944, filed on Aug. 14, 2013.

(56) References Cited

U.S. PATENT DOCUMENTS

| | | | |
|---|---|---|---|
| 4,798,594 A | 1/1989 | Hillstead |
| 4,809,679 A | 3/1989 | Shimonaka et al. |
| 4,857,062 A | 8/1989 | Russell |
| 4,858,810 A | 8/1989 | Intlekofer et al. |
| 4,895,346 A | 1/1990 | Steigerwald |
| 4,895,565 A | 1/1990 | Hillstead |
| 4,929,241 A | 5/1990 | Kulli |
| 4,977,897 A | 12/1990 | Hurwitz |
| 5,009,391 A | 4/1991 | Steigerwald |
| 5,048,530 A | 9/1991 | Hurwitz |
| 5,053,017 A | 10/1991 | Chamuel |
| 5,057,084 A | 10/1991 | Ensminger et al. |
| 5,084,023 A | 1/1992 | Lemieux |
| 5,135,504 A | 8/1992 | McLees |
| 5,176,647 A | 1/1993 | Knoepfler |
| 5,304,156 A | 4/1994 | Sylvanowicz et al. |
| 5,312,359 A | 5/1994 | Wallace |
| 5,318,541 A | 6/1994 | Viera et al. |
| 5,325,746 A | 7/1994 | Anderson |
| 5,350,363 A | 9/1994 | Goode et al. |
| 5,389,100 A | 2/1995 | Bacich et al. |
| 5,405,323 A | 4/1995 | Rogers et al. |
| 5,409,464 A | 4/1995 | Villalobos |
| 5,562,619 A | 10/1996 | Mirarchi et al. |
| 5,611,792 A | 3/1997 | Gustafsson |
| 5,613,663 A | 3/1997 | Schmidt et al. |
| 5,637,096 A | 6/1997 | Yoon |
| 5,704,914 A | 1/1998 | Stocking et al. |
| 5,766,135 A | 6/1998 | Terwilliger |
| 5,769,795 A | 6/1998 | Terwilliger |
| 5,858,007 A | 1/1999 | Fagan et al. |
| 6,050,976 A | 4/2000 | Thorne et al. |
| 6,053,870 A | 4/2000 | Fulton, III |
| 6,117,108 A | 9/2000 | Woehr et al. |
| 6,197,001 B1 | 3/2001 | Wilson et al. |
| 6,228,060 B1 | 5/2001 | Howell |
| 6,287,278 B1 | 9/2001 | Woehr et al. |
| 6,287,280 B1 | 9/2001 | Lampropoulos et al. |
| 6,299,602 B1 | 10/2001 | Miller et al. |
| 6,413,250 B1 | 7/2002 | Smith |
| 6,443,929 B1 | 9/2002 | Kuracina et al. |
| 6,506,181 B2 | 1/2003 | Meng et al. |
| 6,551,282 B1 | 4/2003 | Exline et al. |
| 6,565,542 B2 | 5/2003 | Kumar et al. |
| 6,595,955 B2 | 7/2003 | Ferguson et al. |
| 6,602,240 B2 | 8/2003 | Hermann et al. |
| 6,610,016 B1 | 8/2003 | Violante et al. |
| 6,616,630 B1 | 9/2003 | Woehr et al. |
| 6,626,869 B1 | 9/2003 | Bint |
| 6,629,959 B2 | 10/2003 | Kuracina et al. |
| 6,652,486 B2 | 11/2003 | Bialecki et al. |
| 6,652,490 B2 | 11/2003 | Howell |
| 6,699,221 B2 | 3/2004 | Vaillancourt |
| 6,709,419 B2 | 3/2004 | Woehr |
| 6,719,726 B2 | 4/2004 | Meng et al. |
| 6,749,588 B1 | 6/2004 | Howell et al. |
| 6,796,962 B2 | 9/2004 | Ferguson et al. |
| 6,860,856 B2 | 3/2005 | Ward et al. |
| 6,860,865 B1 | 3/2005 | Feldgiebel |
| 6,902,546 B2 | 6/2005 | Ferguson |
| 6,972,002 B2 | 12/2005 | Thorne |
| 6,984,213 B2 | 1/2006 | Horner et al. |
| 6,986,749 B2 | 1/2006 | Wollschlager |
| 7,004,927 B2 | 2/2006 | Ferguson et al. |
| 7,008,402 B2 | 3/2006 | Ferguson et al. |
| 7,008,404 B2 | 3/2006 | Nakajima |
| 7,044,936 B2 | 5/2006 | Harding et al. |
| 7,179,244 B2 | 2/2007 | Smith et al. |
| 7,186,239 B2 | 3/2007 | Woehr |
| 7,226,434 B2 | 6/2007 | Carlyon et al. |
| 7,247,148 B2 | 7/2007 | Murashita |
| 7,264,613 B2 | 9/2007 | Woehr et al. |
| 7,291,128 B2 | 11/2007 | Rossi et al. |
| 7,291,130 B2 | 11/2007 | McGurk |
| 7,341,573 B2 | 3/2008 | Ferguson et al. |
| 7,347,838 B2 | 3/2008 | Kulli |
| 7,357,784 B2 | 4/2008 | Ferguson |
| 7,374,554 B2 | 5/2008 | Menzi et al. |
| 7,413,562 B2 | 8/2008 | Ferguson et al. |
| 7,458,954 B2 | 12/2008 | Ferguson et al. |
| 7,476,244 B2 | 1/2009 | Buzzard et al. |
| 7,534,227 B2 | 5/2009 | Kulli |
| 7,544,184 B2 | 6/2009 | Cope et al. |
| 7,556,617 B2 | 7/2009 | Voorhees, Jr. et al. |
| 7,597,681 B2 | 10/2009 | Sutton et al. |
| 7,604,616 B2 | 10/2009 | Thoresen et al. |
| 7,608,057 B2 | 10/2009 | Woehr et al. |
| 7,611,485 B2 | 11/2009 | Ferguson |
| 7,611,499 B2 | 11/2009 | Woehr et al. |
| 7,618,395 B2 | 11/2009 | Ferguson |
| 7,625,360 B2 | 12/2009 | Woehr et al. |
| 7,632,243 B2 | 12/2009 | Bialecki et al. |
| 7,635,352 B2 | 12/2009 | Adams |
| 7,637,893 B2 | 12/2009 | Christensen et al. |
| 7,651,476 B2 | 1/2010 | Kohler |
| 7,670,317 B2 | 3/2010 | Cindrich et al. |
| 7,682,331 B2 | 3/2010 | Carrez et al. |
| 7,682,344 B2 | 3/2010 | Barrelle |
| 7,691,088 B2 | 4/2010 | Howell |
| 7,713,243 B2 | 5/2010 | Hillman |
| 7,731,687 B2 | 6/2010 | Menzi et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,340 B2 | 6/2010 | Harding et al. |
| 7,744,568 B2 | 6/2010 | Douglas et al. |
| 7,753,877 B2 | 7/2010 | Bialecki et al. |
| 7,762,993 B2 | 7/2010 | Perez |
| 7,806,849 B2 | 10/2010 | Woehr |
| 7,828,774 B2 | 11/2010 | Harding et al. |
| 7,833,199 B2 | 11/2010 | Franer et al. |
| 7,938,805 B2 | 5/2011 | Harding et al. |
| 7,951,121 B2 | 5/2011 | Weaver et al. |
| 7,967,829 B2 | 6/2011 | Gunderson et al. |
| 7,972,313 B2 | 7/2011 | Woehr et al. |
| 7,976,502 B2 | 7/2011 | Baid |
| 7,988,664 B2 | 8/2011 | Fiser et al. |
| 8,038,647 B2 | 10/2011 | Harding et al. |
| 8,048,039 B2 | 11/2011 | Carlyon et al. |
| 8,052,647 B2 | 11/2011 | Raulerson et al. |
| 8,066,675 B2 | 11/2011 | Cindrich et al. |
| 8,162,881 B2 | 4/2012 | Lilley, Jr. et al. |
| 8,162,939 B2 | 4/2012 | Shizuka |
| 8,177,772 B2 | 5/2012 | Christensen et al. |
| 8,211,070 B2 | 7/2012 | Woehr et al. |
| 8,235,971 B2 | 8/2012 | Christensen et al. |
| 8,251,950 B2 | 8/2012 | Albert et al. |
| 8,257,315 B2 | 9/2012 | Franer et al. |
| 8,273,056 B2 | 9/2012 | Kuracina et al. |
| 8,292,852 B2 | 10/2012 | Mulholland et al. |
| 8,298,181 B2 | 10/2012 | Perez |
| 8,328,762 B2 | 12/2012 | Woehr et al. |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,348,893 B2 | 1/2013 | Carlyon |
| 8,369,935 B2 | 2/2013 | Ryan |
| 8,382,721 B2 | 2/2013 | Woehr et al. |
| 8,403,886 B2 | 3/2013 | Bialecki et al. |
| 8,449,530 B2 | 5/2013 | Bacher et al. |
| 8,460,247 B2 | 6/2013 | Woehr et al. |
| 8,480,627 B2 | 7/2013 | Christiansen |
| 8,486,024 B2 | 7/2013 | Steube |
| 8,500,696 B2 | 8/2013 | Kobayashi et al. |

(56) References Cited

U.S. PATENT DOCUMENTS

| | | |
|---|---|---|
| 8,506,528 B2 | 8/2013 | Fiser et al. |
| 8,523,819 B2 | 9/2013 | Abe et al. |
| 8,535,271 B2 | 9/2013 | Fuchs et al. |
| 8,540,728 B2 | 9/2013 | Woehr et al. |
| 8,647,301 B2 | 2/2014 | Bialecki et al. |
| 9,011,351 B2 | 4/2015 | Hoshinouchi |
| 9,126,017 B2 | 9/2015 | Albert et al. |
| 9,717,886 B2 | 8/2017 | Kuehn et al. |
| 2002/0026151 A1 | 2/2002 | Miller et al. |
| 2004/0106891 A1 | 6/2004 | Langan et al. |
| 2004/0127855 A1 | 7/2004 | Core |
| 2005/0075609 A1 | 4/2005 | Latona |
| 2005/0096592 A1 | 5/2005 | Carlyon et al. |
| 2006/0155245 A1* | 7/2006 | Woehr .............. A61M 39/0693 604/164.08 |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038187 A1 | 2/2007 | Albert et al. |
| 2007/0073221 A1 | 3/2007 | Bialecki et al. |
| 2007/0073270 A1 | 3/2007 | Christensen et al. |
| 2007/0156093 A1 | 7/2007 | Woehr |
| 2007/0270753 A1 | 11/2007 | Kulli |
| 2008/0065015 A1 | 3/2008 | Fiser et al. |
| 2008/0300574 A1 | 12/2008 | Belson et al. |
| 2009/0082732 A1 | 3/2009 | Hillman |
| 2009/0143738 A1 | 6/2009 | Hendriksen et al. |
| 2009/0163861 A1 | 6/2009 | Carlyon |
| 2009/0163871 A1 | 6/2009 | Burkholz et al. |
| 2009/0177114 A1 | 7/2009 | Chin et al. |
| 2009/0247986 A1 | 10/2009 | Rioux et al. |
| 2009/0247994 A1 | 10/2009 | Bacher et al. |
| 2009/0299291 A1 | 12/2009 | Baid |
| 2009/0312711 A1 | 12/2009 | Brimhall |
| 2010/0042076 A1 | 2/2010 | McCarthy et al. |
| 2010/0087755 A1 | 4/2010 | Boezaart |
| 2010/0094310 A1* | 4/2010 | Warring ............ A61M 25/0606 606/108 |
| 2010/0168756 A1 | 7/2010 | Dorn et al. |
| 2010/0191188 A1 | 7/2010 | Harding et al. |
| 2010/0191189 A1 | 7/2010 | Harding et al. |
| 2010/0191224 A1 | 7/2010 | Butcher |
| 2010/0204654 A1 | 8/2010 | Mulholland et al. |
| 2010/0249707 A1 | 9/2010 | Woehr et al. |
| 2011/0009849 A1 | 1/2011 | Christensen et al. |
| 2011/0213307 A1 | 9/2011 | Kawai et al. |
| 2011/0282280 A1 | 11/2011 | Fiser et al. |
| 2011/0282285 A1 | 11/2011 | Blanchard et al. |
| 2011/0288482 A1 | 11/2011 | Farrell et al. |
| 2011/0319825 A1 | 12/2011 | Goral et al. |
| 2011/0319838 A1 | 12/2011 | Goral et al. |
| 2012/0053523 A1 | 3/2012 | Harding |
| 2012/0059247 A1 | 3/2012 | Speeg et al. |
| 2012/0078200 A1 | 3/2012 | Woehr et al. |
| 2012/0089094 A1 | 4/2012 | Franer et al. |
| 2012/0095404 A1 | 4/2012 | Massengale et al. |
| 2012/0116248 A1 | 5/2012 | Mcweeney et al. |
| 2012/0123339 A1 | 5/2012 | Abe et al. |
| 2012/0172806 A1 | 7/2012 | Woehr et al. |
| 2012/0179104 A1 | 7/2012 | Woehr et al. |
| 2012/0184910 A1 | 7/2012 | Woehr |
| 2012/0197200 A1 | 8/2012 | Belson |
| 2012/0203181 A1 | 8/2012 | Woehr et al. |
| 2012/0215171 A1 | 8/2012 | Christiansen |
| 2012/0220942 A1 | 8/2012 | Hall et al. |
| 2012/0220956 A1 | 8/2012 | Kuracina et al. |
| 2012/0271235 A1 | 10/2012 | Fuchs et al. |
| 2012/0271247 A1 | 10/2012 | Weaver et al. |
| 2012/0277679 A1 | 11/2012 | Steube |
| 2012/0283553 A1 | 11/2012 | Cully et al. |
| 2013/0006101 A1 | 1/2013 | McHugo et al. |
| 2013/0030372 A1 | 1/2013 | Franer et al. |
| 2013/0046315 A1 | 2/2013 | Woehr et al. |

FOREIGN PATENT DOCUMENTS

| | | |
|---|---|---|
| CN | 102440840 A | 5/2012 |
| CN | 102458553 A | 5/2012 |
| CN | 102939129 A | 2/2013 |
| EP | 0386936 A1 | 9/1990 |
| EP | 2433670 A1 | 3/2012 |
| JP | 2008148737 A | 7/2008 |
| JP | 2010-512803 A | 4/2010 |
| JP | 2013-529111 A | 7/2013 |
| WO | 9912474 A1 | 3/1999 |
| WO | 2007/003874 A1 | 1/2007 |
| WO | 2007/006055 A2 | 1/2007 |
| WO | 2008/005618 A2 | 1/2008 |
| WO | 2010/012023 A1 | 2/2010 |
| WO | 2010/078151 A1 | 7/2010 |
| WO | 2011/143621 A1 | 11/2011 |
| WO | 2012/162677 A1 | 11/2012 |
| WO | 2015/023358 A1 | 2/2015 |

OTHER PUBLICATIONS

Office Action issued in Chinese Application No. 201480053619.7, dated Jun. 1, 2018.

* cited by examiner

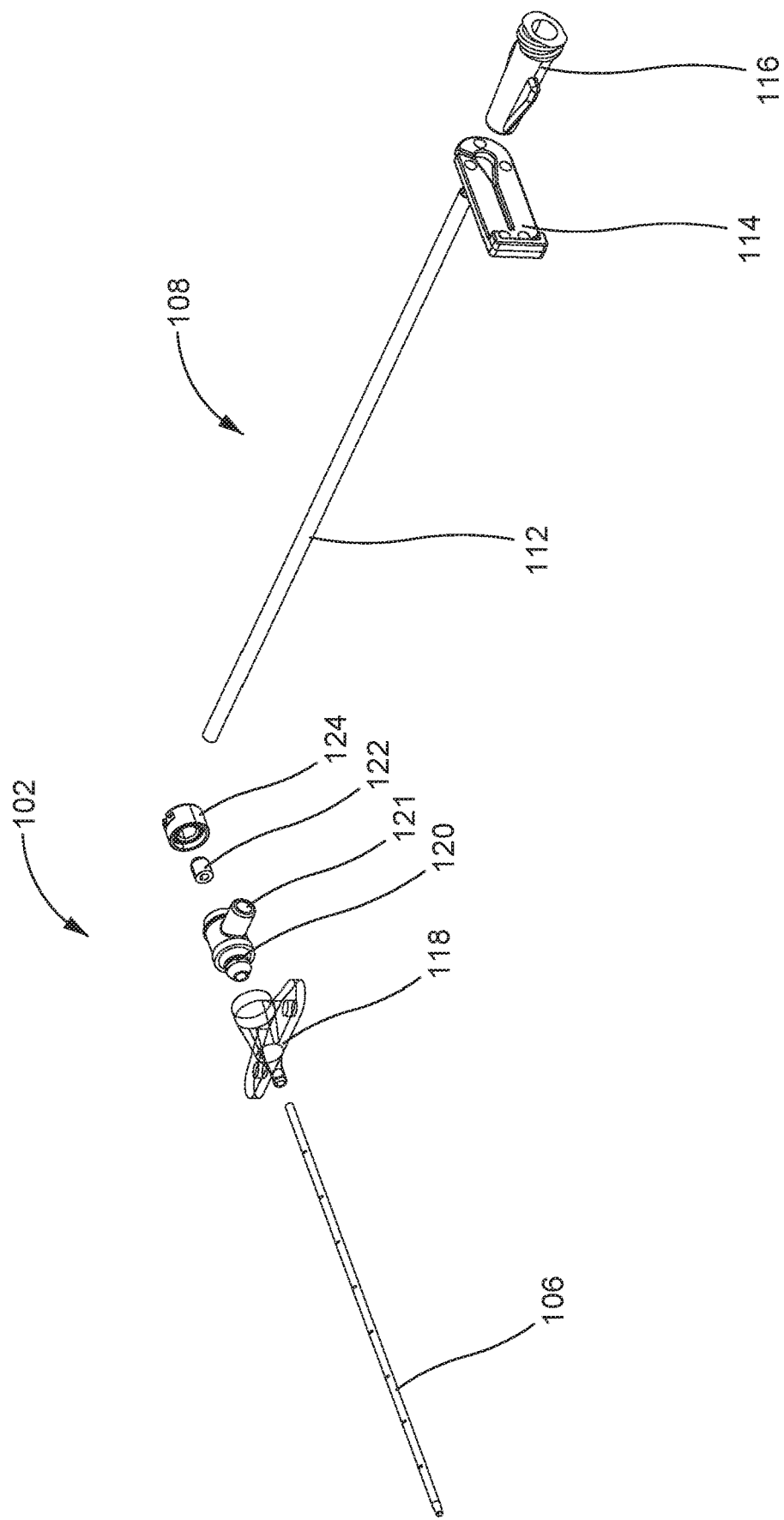

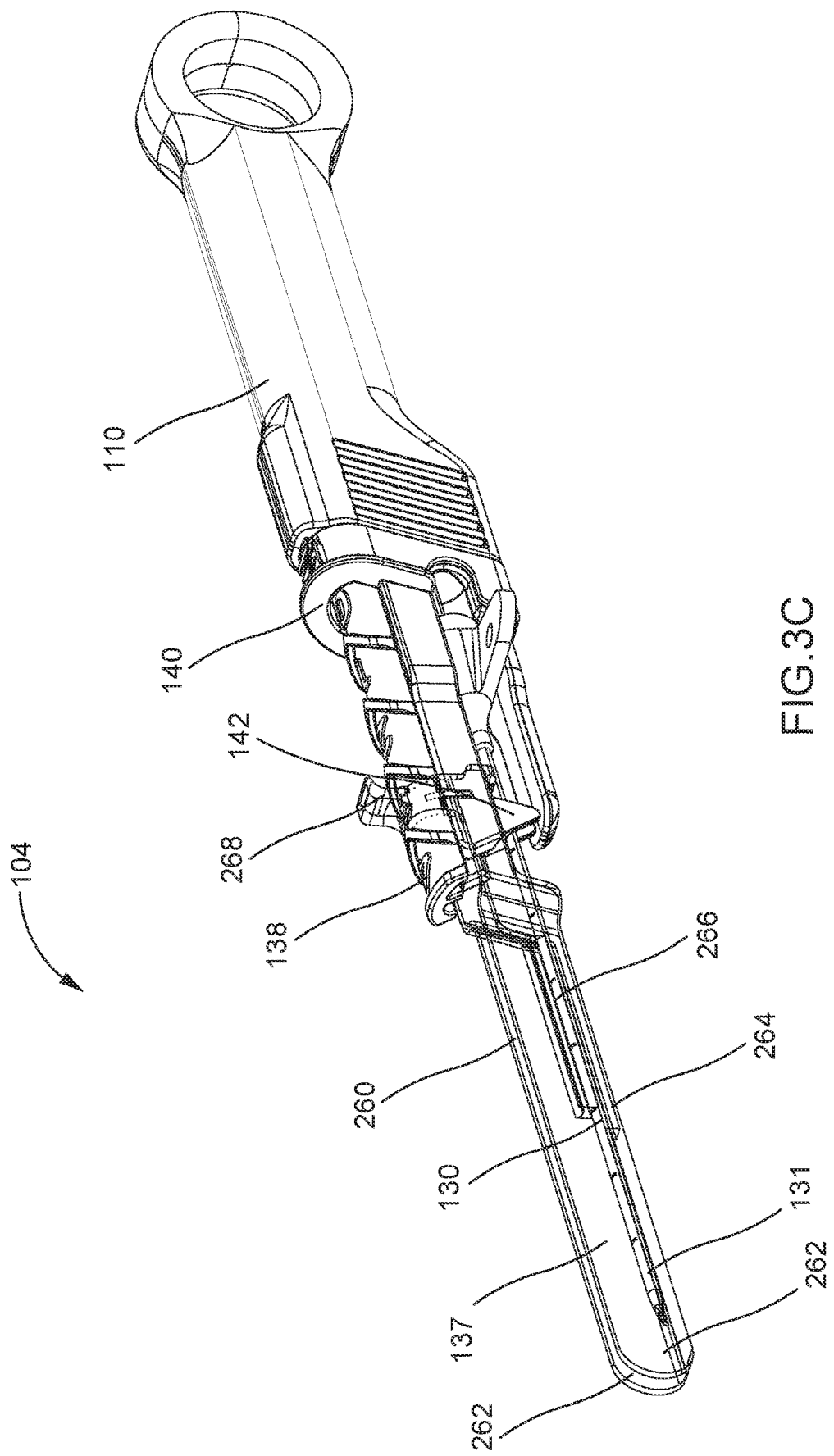

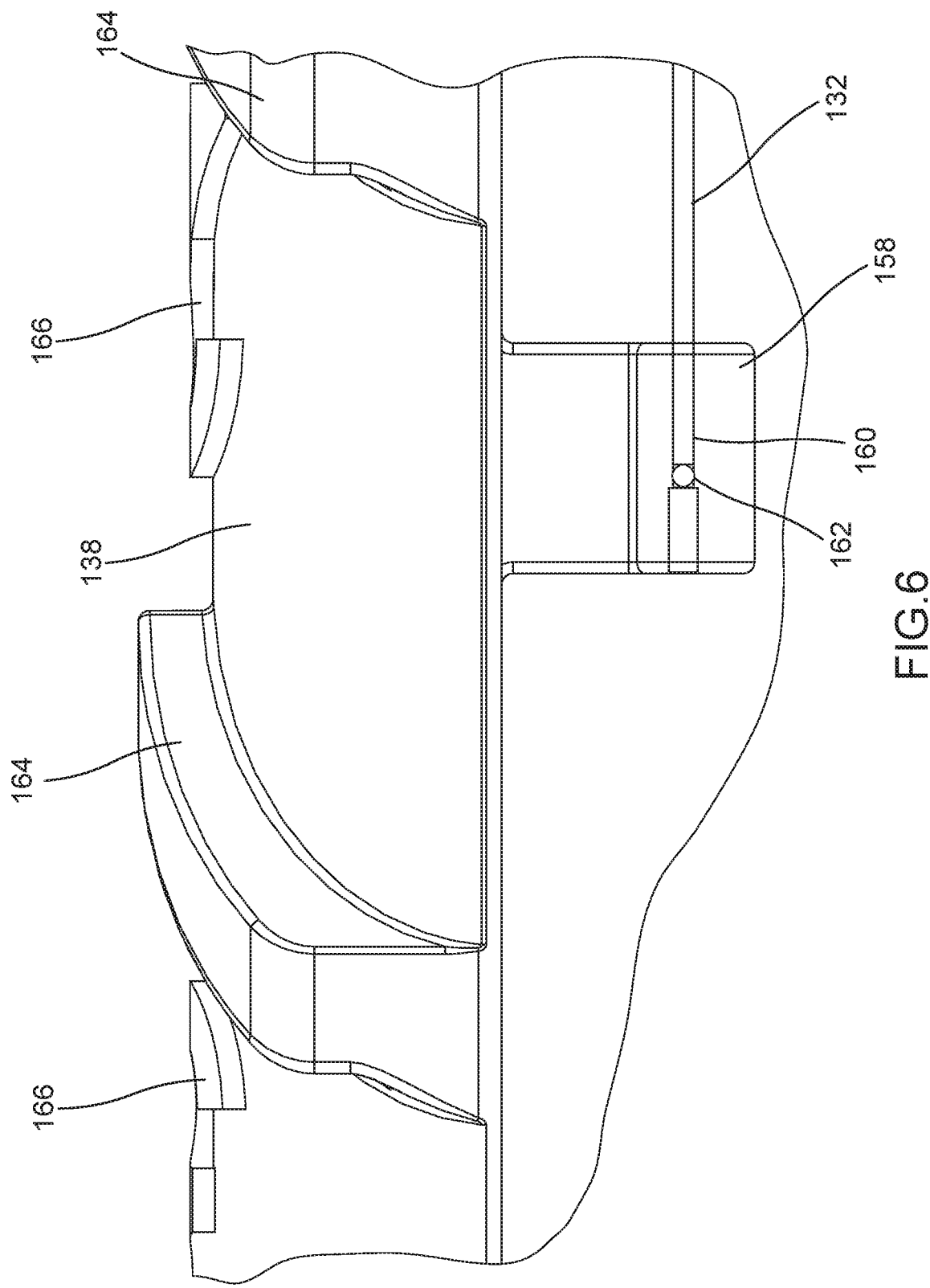

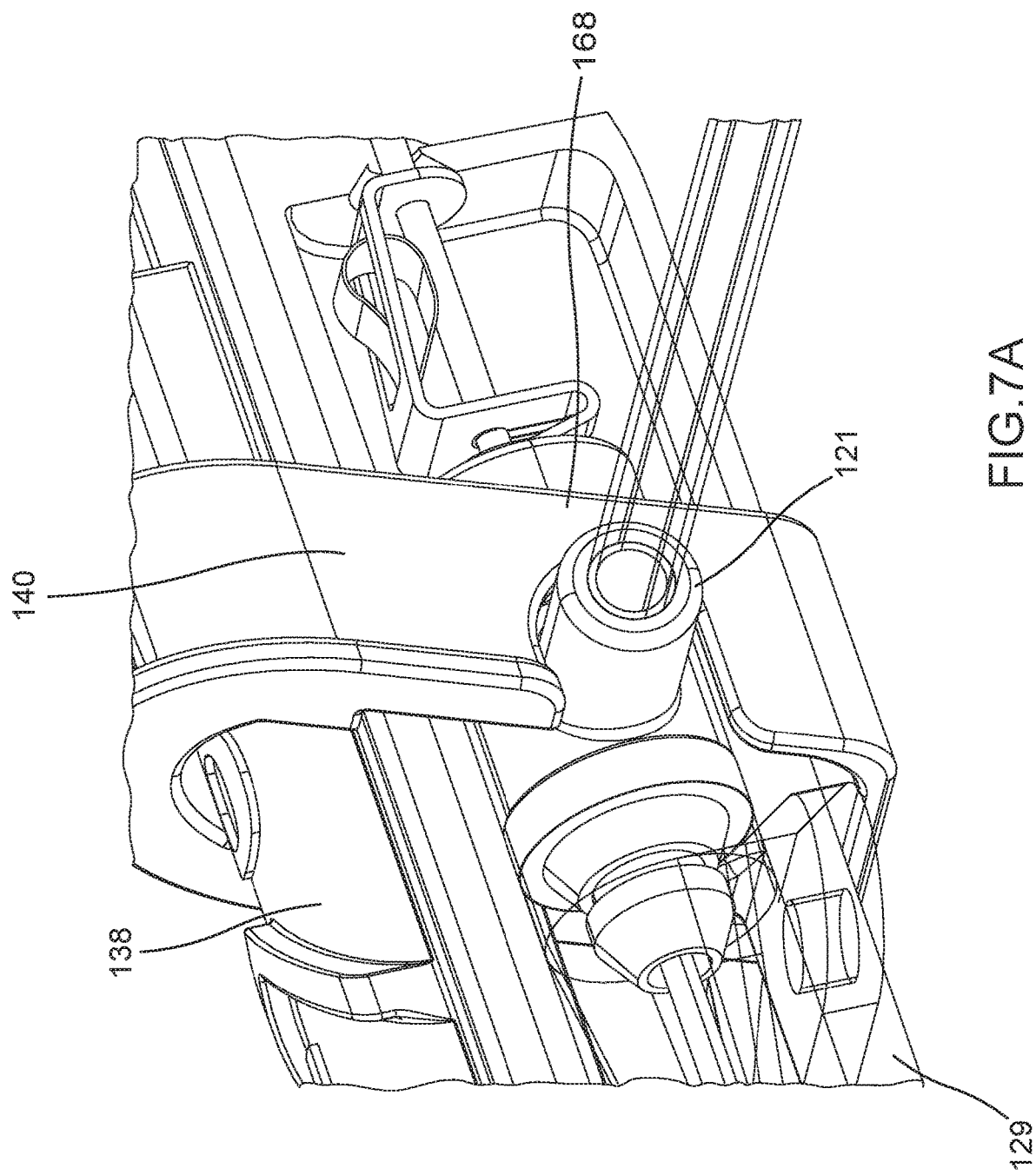

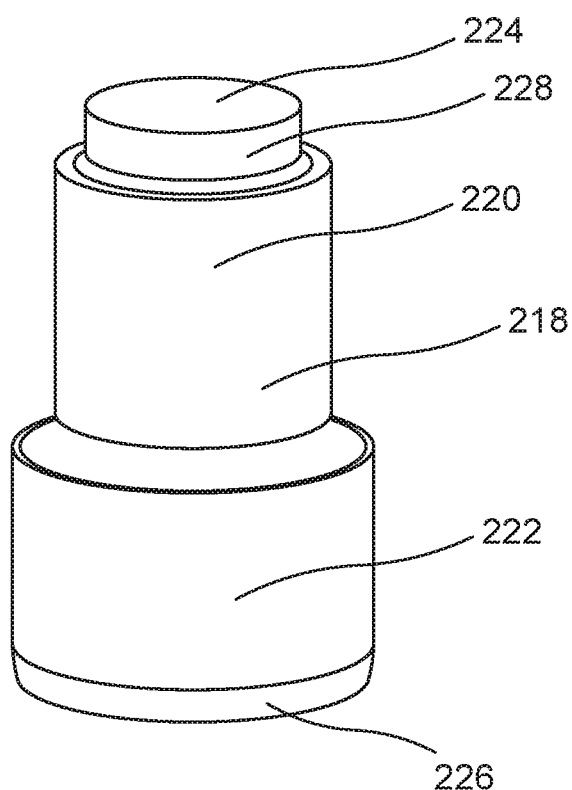
FIG.13A
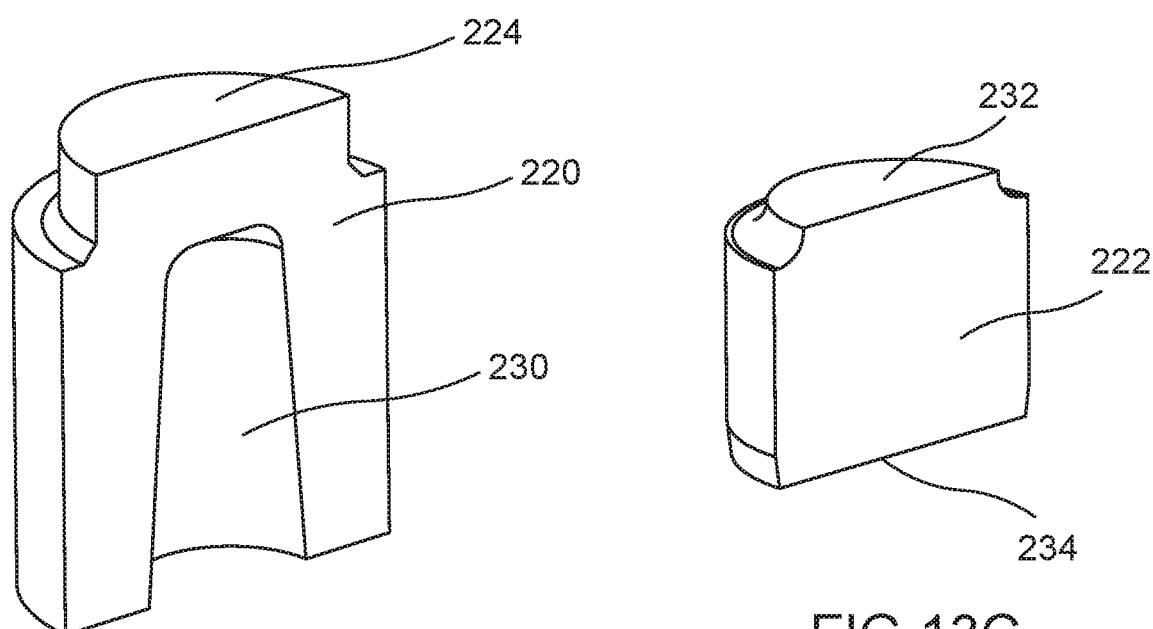
FIG.13B
FIG.13C

CATHETER INSERTION DEVICE

CROSS REFERENCE TO RELATED APPLICATION

This application is a divisional of U.S. patent application Ser. No. 14/306,698, filed Jun. 17, 2014, which is a continuation-in-part of U.S. patent application Ser. No. 14/205,307, filed Mar. 11, 2014, now U.S. Pat. No. 9,717,886, which claims the benefit of U.S. Provisional Application No. 61/778,302, filed on Mar. 12, 2013, and also claims the benefit of U.S. Provisional Application No. 61/865,944, filed on Aug. 14, 2013, the disclosures of which are hereby incorporated by reference in their entireties.

TECHNICAL FIELD

This disclosure generally relates to medical devices for use in insertion of catheters or other medical equipment into the vasculature of a patient. More particularly, this disclosure relates to a catheter insertion device for at least partial insertion of a catheter within the vasculature of the patient.

BACKGROUND

Different types of medical devices, such as needles, introducers, trocars, catheters, stents, angiography balloons, cutting tools, and imaging tools can be introduced into the body for various medical procedures. For example, catheters are used to introduce or remove fluids from vessels in the body for a variety of medical procedures. In a typical procedure, to insert a catheter in a vessel, the vessel access is first verified by aspiration using a long hollow needle, such as a syringe needle. A guidewire is then passed through the needle into the vessel. The guidewire acts as a track for the catheter to pass over to reach a target location within the vessel. A catheter is finally passed over the guidewire to the target location in the vasculature of the patient. With the catheter in place, the needle and the guidewire are removed, leaving only the catheter in the vessel. Fluids are then introduced or removed from the vessel through the catheter by connecting a fluid source or aspiration device to the catheter hub.

Various devices are known for placement of a catheter in the vasculature of a patient. The maintenance of sterility of the various components of the device by, for example, preventing the contact of the fingers of the operator with the various parts of the needle, the guidewire and the catheter itself during operation, is important for use of these devices. However, known catheter placement devices typically require the use of two hands for the insertion of the guide wire and advancement of the catheter into the vasculature, which increases the risk of contamination, increases the risk of inadvertently damaging the vessel due to unintended needle point movement, prevents the continuous use of ultrasound from the point of skin penetration, vessel access, wire guide insertion, through to having the first distal portion of the catheter in the vessel and needle point shielded, and makes the device less convenient for use.

Therefore, a need exists for a novel catheter insertion device that allows for single-handed insertion of the catheter within the vasculature of the patient.

SUMMARY

The foregoing needs are met, to a great extent, by implementations of the catheter insertion device according to this disclosure. In accordance with one implementation, a catheter insertion device includes a handle, a needle cannula partially within the handle, a guidewire partially within the handle and the needle cannula, and a first actuator connected to the handle and the guidewire. The needle cannula includes a sharp distal tip extending distally from the handle. The first actuator is movable relative to the handle to move the guidewire relative to the handle, such that moving the first actuator in a proximal direction relative to the handle causes a distal end of the guidewire to move in a distal direction away from the handle, and moving the first actuator in a distal direction relative to the handle causes the distal end of the guidewire to move in a proximal direction towards the handle.

In some implementations, the first actuator can be a slider which is moved by sliding over a portion of the handle, and the first actuator can include an arm extending downward from the bottom surface of the first actuator. The arm can be connected to a proximal end of the guidewire. The arm can include a through hole, where the proximal end of the guidewire can be secured within the through hole. The proximal end of the guidewire can include a ball, where the diameter of the ball can be greater than the diameter of the through hole, such that the guidewire can secured within the through hole by an interference fit.

In some implementations, the handle can include a looped proximal end portion that can define a channel that holds a portion of the guidewire. The catheter insertion device can also include a catheter assembly removably connected to the handle, where the catheter assembly can include an elongated catheter connected to a catheter hub. The catheter insertion device can also include a needle safety clip that can cover the sharp distal tip of the needle cannula following removal of the needle cannula from the catheter hub. The catheter hub can house a hemostasis valve. The hemostasis valve can include a distal piece and a proximal piece that when mated define a closed inner cavity. The volume of the closed inner cavity defined by the proximal piece can be greater than any volume of the inner cavity defined by the distal piece.

In some implementations, the catheter insertion device can also include a second actuator connected to the handle, where the second actuator can be movable relative to the handle to push the catheter group relative to the handle. The second actuator can include a notch to receive a portion of the catheter hub. The second actuator can include an enlarged proximal end that engages with the handle to limit travel of the second actuator relative to the handle.

In some implementations, the catheter insertion device can also include a needle support connected to the handle, where the needle support can stabilize an intermediate portion of the needle cannula during insertion of the needle cannula into a patient. The intermediate portion of the needle cannula can freely extend from the handle. The needle support can include a top portion that abuts a bottom surface of the first actuator to prevent movement of the needle support relative to the handle.

According to another implementation, a catheter insertion device includes an insertion group including a handle, a needle cannula partially within the handle, and a needle support connected to the handle. The catheter insertion device also includes a catheter group comprising an elongated catheter and a catheter hub connected to the proximal end of the elongated catheter. The needle support includes two parallel features separated by a distance greater than an outer diameter of the elongated catheter to stabilize the needle cannula during insertion of the needle cannula into a patient. The needle cannula has a cantilever portion extending from the handle, where the needle support supports the needle cannula on the cantilever portion.

In some implementations, the needle support can move relative to the handle upon abutment of the catheter hub to the needle support. The needle support can move relative to the handle by swinging upward or downward relative to the handle. The two parallel features can be two parallel walls. The handle can include a top arm, and the needle support can be connected to a distal region of the top arm of the handle.

According to another implementation, a method of using a catheter insertion device is disclosed. Initially, a practitioner receives the catheter insertion device. The catheter insertion device includes a handle, a needle cannula partially within the handle, a guidewire partially within the handle and the needle cannula, a first actuator connected to the handle and the guidewire, a catheter group removably connected to the handle, and a second actuator connected to the handle. The needle cannula includes a sharp distal tip extending distally from the handle. The first actuator is movable relative to the handle to move the guidewire relative to the handle. The catheter group includes an elongated catheter and a catheter hub connected to the proximal end of the elongated catheter. The second actuator is movable relative to the handle to move the catheter group relative to the handle.

Next, the practitioner grips the handle using a hand of the practitioner. The practitioner then navigates the handle until the sharp distal tip of the needle cannula is within the vasculature of a patient. Next, the practitioner actuates the first actuator using a first finger to cause a distal tip of the guidewire to move in a distal direction relative to the handle and within the vasculature of the patient. Finally, the practitioner actuates the second actuator using the first finger of the practitioner to cause the catheter group to move in a distal direction relative to the handle so that the distal end of the elongated catheter is inserted within the vasculature of the patient.

In some implementations, the handle can include a first side and a second side opposite the first side. The practitioner can then grip the first side using a second finger of the hand of the practitioner and grip the second side using a third, different finger of the hand of the practitioner. The first actuator can be actuated in a proximal direction using the first finger of the hand of the practitioner to cause a distal tip of the guidewire to move in a distal direction relative to the handle and within the vasculature of the patient, and the second actuator can be actuated in a distal direction using the first finger of the practitioner to cause the catheter group to move in a distal direction relative to the handle so that the distal end of the elongated catheter is inserted within the vasculature of the patient.

In some implementations, the practitioner can grip the catheter hub with his other hand while pulling the handle in a proximal direction to separate the catheter group from the handle. The practitioner can grip the handle overhand, such that the first finger can be the index finger of the hand of the practitioner. The practitioner can grip the handle underhand, such that the first finger can be the index finger of the hand of the practitioner.

According to another implementation, a method of inserting a catheter is disclosed. Initially, a catheter insertion device is received. The catheter insertion device includes a handle, a needle cannula partially within the handle, a guidewire partially within the handle and the needle cannula, a first actuator connected to the handle and the guidewire, a catheter group removably connected to the handle, and a second actuator connected to the handle. The needle cannula includes a sharp distal tip extending distally from the handle. The first actuator is movable relative to the handle to move the guidewire relative to the handle. The catheter group includes an elongated catheter and a catheter hub connected to the proximal end of the elongated catheter. The second actuator is movable relative to the handle to move the catheter group relative to the handle.

Next, the first actuator is actuated using a finger to cause a distal tip of the guidewire to move in a distal direction relative to the handle and within the vasculature of the patient. The second actuator is actuated using the same finger to cause the catheter group to move in a distal direction relative to the handle so that the distal end of the elongated catheter is inserted within the vasculature of the patient.

Certain implementations of the catheter insertion device have been outlined so that the detailed description below may be better understood. There are, of course, additional implementations that will be described below and which will form the subject matter of the claims.

In this respect, before explaining at least one implementation in detail, it is to be understood that the catheter insertion device is not limited in its application to the details of construction and to the arrangements of the components set forth in the following disclosure or illustrated in the drawings. Also, it is to be understood that the phraseology and terminology employed herein, as well as in the Abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the catheter insertion device. It is understood, therefore, that the claims include such equivalent constructions insofar as they do not depart from the spirit and scope of the present disclosure.

BRIEF DESCRIPTION OF THE DRAWINGS

FIG. 2A illustrates an exploded view of the separate components of the catheter group of the catheter insertion device.

FIG. 3C illustrates a perspective view of an assembled insertion group of the catheter insertion device having another implementation of the needle guard.

FIG. 6 illustrates a transparent side view of a portion of a slider of the insertion group of the catheter insertion device.

FIG. 7A illustrates the left side of a release of the insertion group of the catheter insertion device.

FIG. 13A illustrates a perspective view of a second implementation of a valve having two parts. FIG. 13B illustrates a proximal part of the two-part valve. FIG. 13C illustrates a distal part of the two-part valve.

Implementations of the catheter insertion device are described with reference to the drawings, in which like reference numerals refer to like parts throughout.

DETAILED DESCRIPTION

Figure 1:
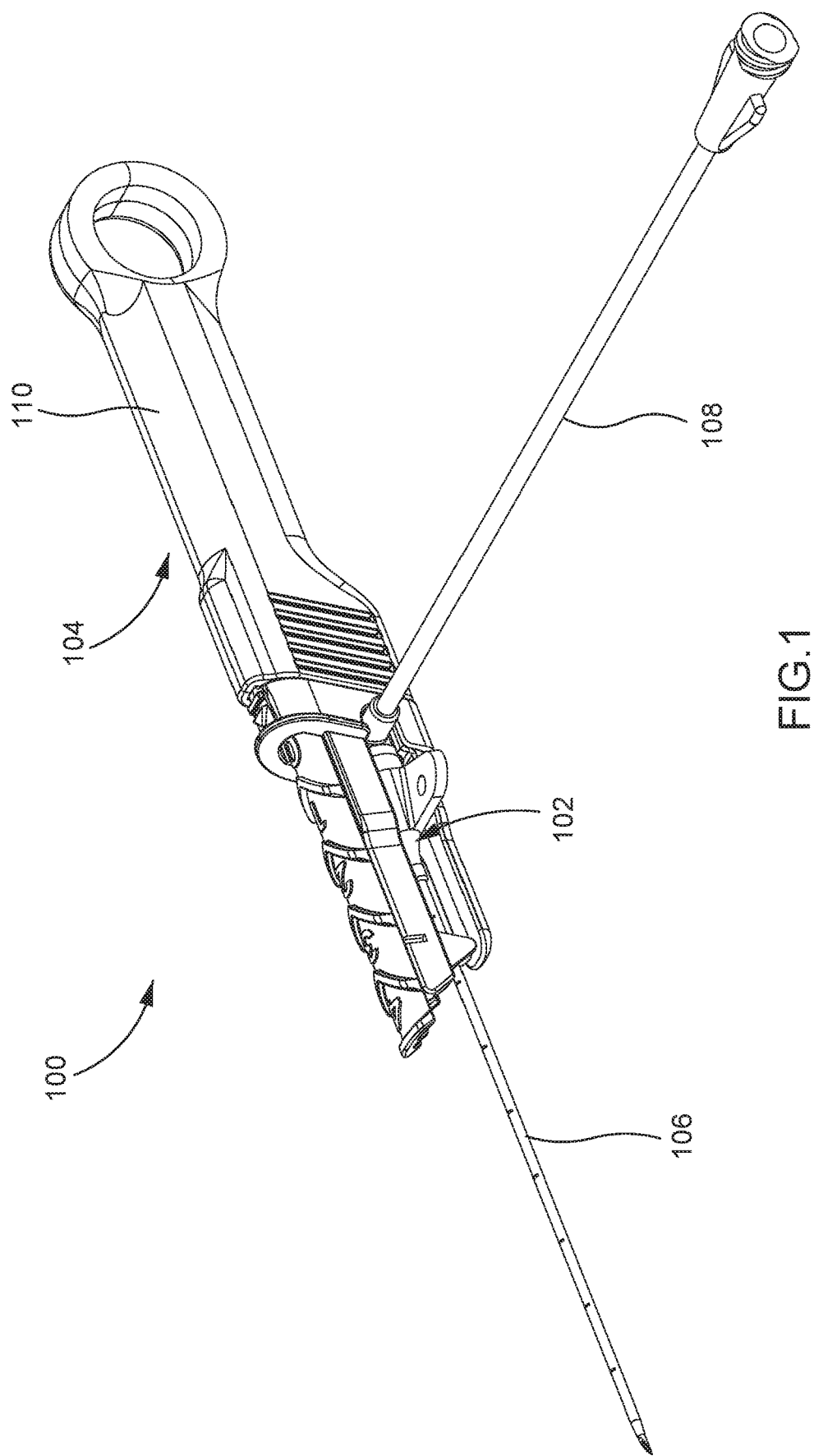
FIG. 1 illustrates a perspective view of an implementation of a catheter insertion device including a catheter group and an insertion group.

Referring to FIG. 1, a perspective view of an implementation of a catheter insertion device 100 including a catheter group 102 and an insertion group 104 is illustrated. The insertion group 104 can be separated from the catheter group 102 following partial insertion of a catheter 106 in the vasculature of a patient. The catheter group 102 also includes an extension line assembly 108 in fluid communication with the catheter 106. The extension line assembly 108 can be connected to a fluid source or an aspiration device. The insertion group 104 includes a handle 110 that is initially connected to the catheter group 102 and that facilitates the insertion of the catheter 106 in the vasculature of the patient.

Figure 2B:
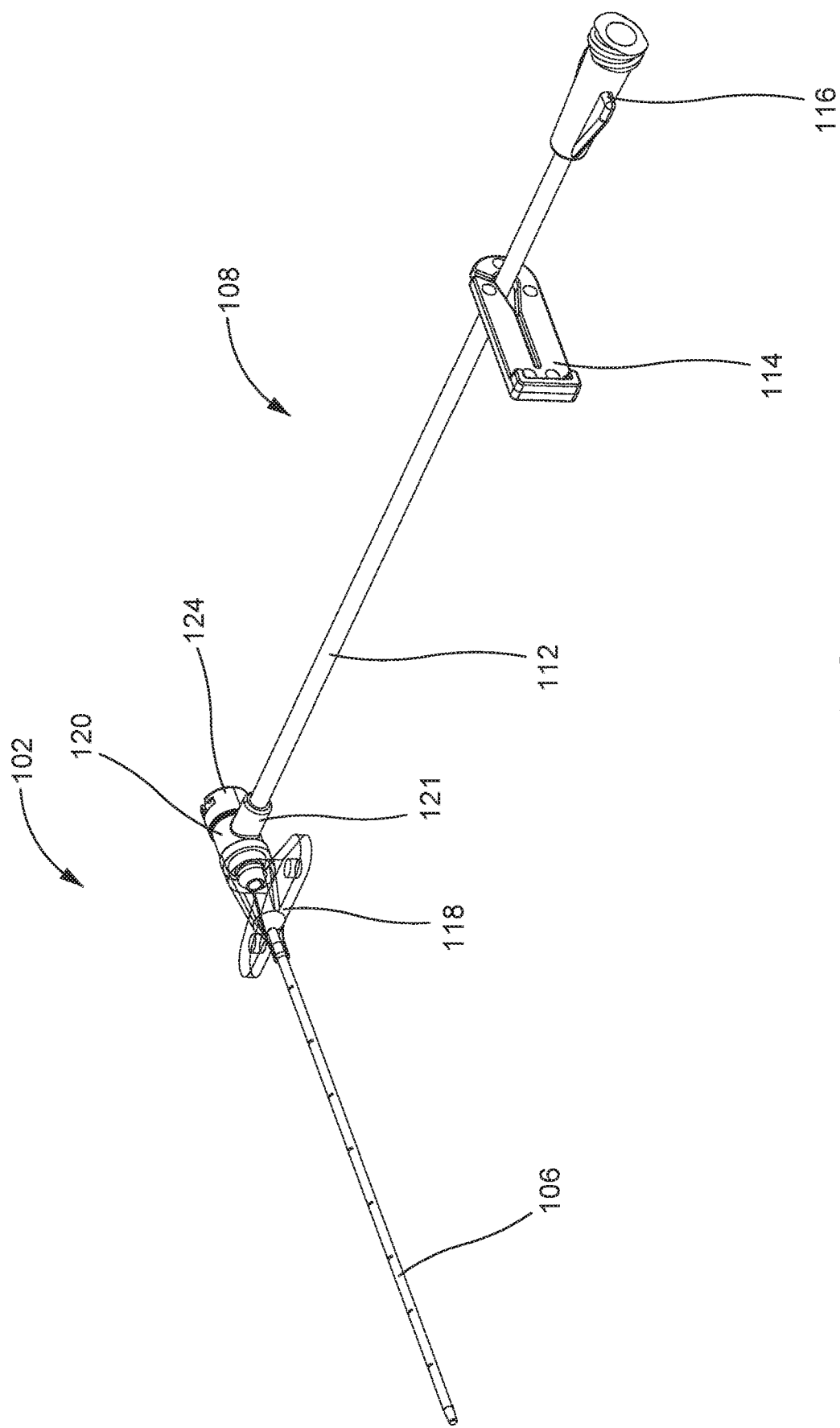
FIG. 2B illustrates a partially transparent perspective view of the assembled catheter group of the catheter insertion device.

Referring to FIG. 2A, an exploded view of the separate components of the catheter group 102 of the catheter insertion device 100 is illustrated. Referring to FIG. 2B, a partially transparent perspective view of the assembled catheter group 102 of the catheter insertion device 100 is illustrated. At its proximal region, the catheter group 102 includes an extension line assembly 108 that includes an elongated extension line 112, an extension line clamp 114, and an extension line hub 116. The elongated extension line 112 defines an elongated lumen that is in fluid communication with the lumen defined by the catheter 106 through the lumen defined by a rigid hub 120. The extension line clamp 114 is received around the elongated extension line 112 and can be slid in a direction perpendicular to the longitudinal axis of the elongated extension line 112 to pinch the elongated extension line 112 closed. When the extension line clamp 114 pinches the elongated extension line 112, fluid is prevented from flowing beyond the extension line clamp 114 either distally towards the catheter 106 or proximally towards the extension line hub 116. The extension line hub 116 defines a lumen that is in fluid communication with the lumen defined by the elongated extension line 112.

In some implementations, the lumen defined by the extension line hub 116 can be tapered from its proximal end towards its distal end, while in other implementations, the lumen defined by the extension line hub 116 can have a uniform diameter. The proximal end of the extension line hub 116 includes a connector, such as a threaded luer lock illustrated in FIG. 2, for connection to a fluid source or an aspiration device. The fluid source can be, for example, a syringe or an intravenous bag.

At its distal end, the catheter group 102 includes the elongated catheter 106 that is connected to a juncture hub 118. In particular, the proximal end of the elongated catheter 106 connects to the distal end of the juncture hub 118. The rigid hub 120 is partially received within the proximal end of the juncture hub 118. The rigid hub 120 receives a seal, such as a valve 122, within an internal cavity defined by the rigid hub 120. The proximal end of the rigid hub 120 is sealed by a rigid hub cap 124. The proximal end of the rigid hub cap 124 has an opening that allows the needle cannula 130 and the guidewire 132 to pass through the rigid hub cap 124 to the valve 122. The elongated catheter 106 defines an elongated lumen that is at least partially received within the vasculature of the patient. The juncture hub 118 defines a tapered cavity that is in fluid communication with the lumen defined by the elongated catheter 106 and the lumen defined by the rigid hub 120. The rigid hub 120 also includes a side port 121 for receiving the elongated extension line 112 of the extension line assembly 108. The lumen defined by the side port 121 is in fluid communication with the lumen defined by the elongated extension line 112.

The valve 122 can be a one-piece valve or a multiple piece valve, as described in greater detail below. When the catheter group 102 is assembled, the valve 122 is enclosed by the rigid hub 120 and the rigid hub cap 124. In some implementations, the catheter group 102 may not include the extension line assembly 108 and the fluid source or aspiration device can be connected to a proximal end of the rigid hub 120.

Figure 3A:
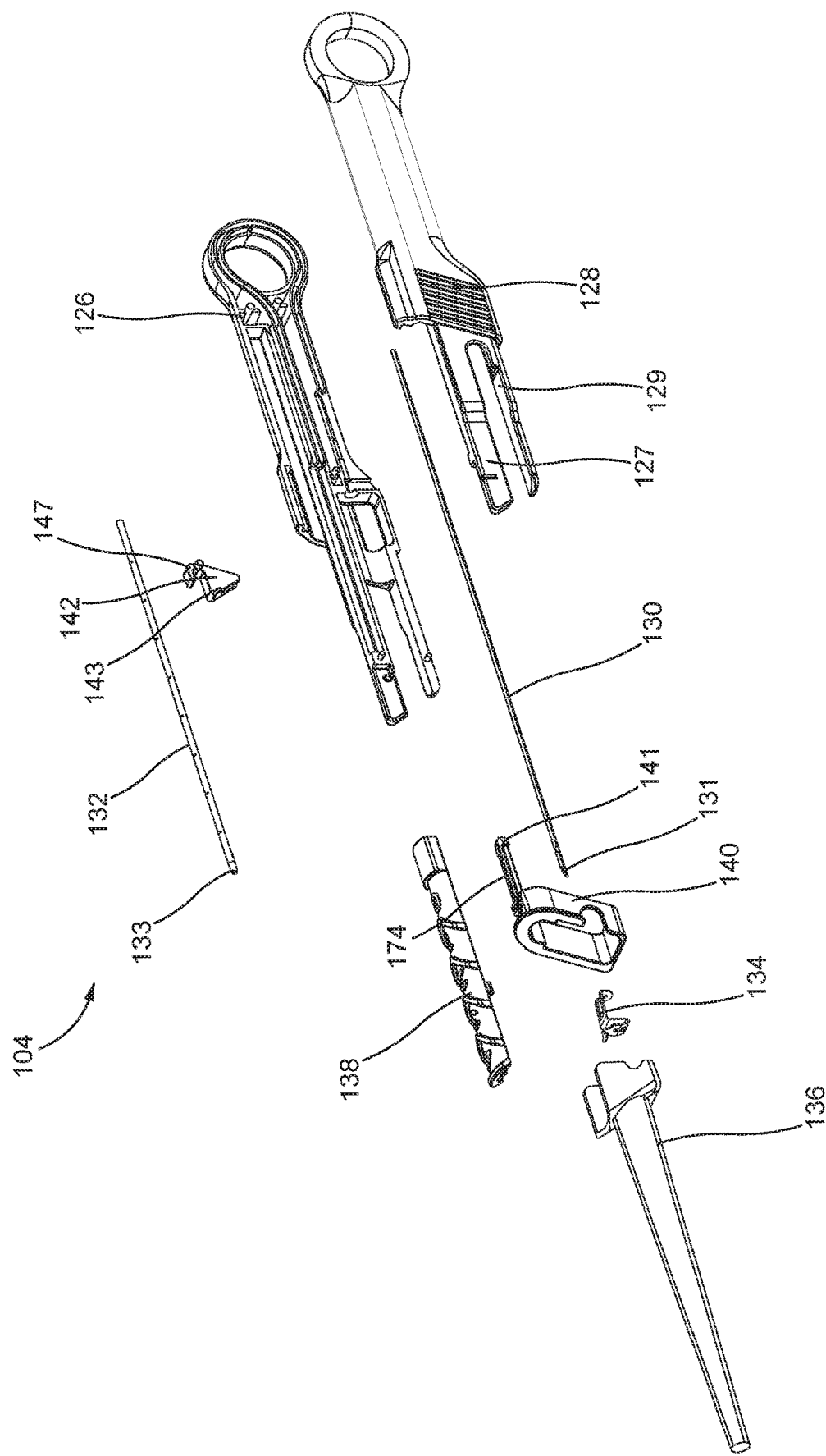
FIG. 3A illustrates an exploded view of the separate components of the insertion group of the catheter insertion device.
Figure 3B:
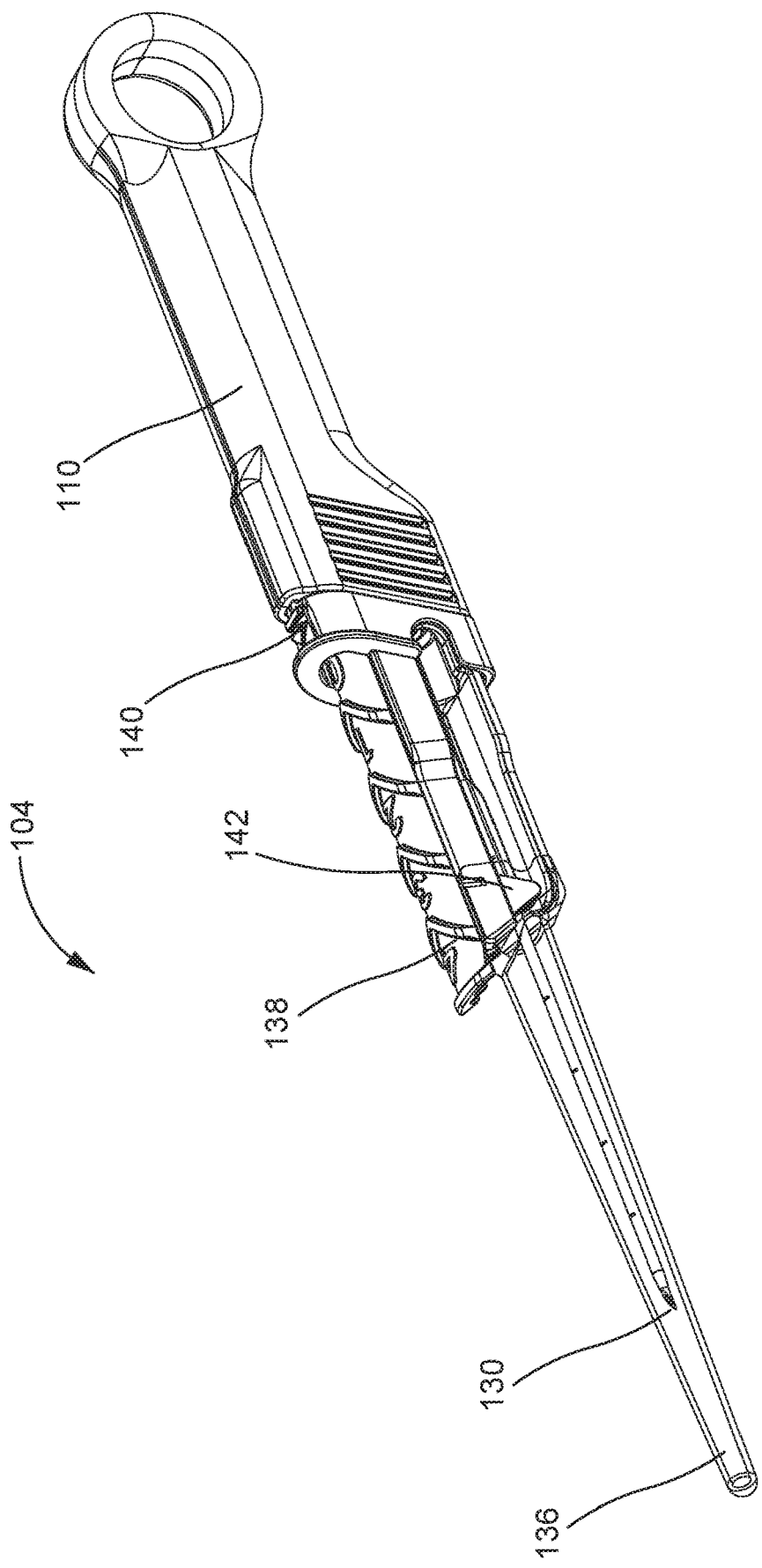
FIG. 3B illustrates a perspective view of the assembled insertion group of the catheter insertion device.

Referring to FIG. 3A, an exploded view of the separate components of the insertion group 104 of the catheter insertion device 100 is illustrated. Referring to FIG. 3B, a perspective view of the assembled insertion group 104 of the catheter insertion device 100 is illustrated. The insertion group 104 includes the handle 110 that is made up of a right housing 126 and a left housing 128 that are connected together. Top arm 127 and bottom arm 129 are formed in the distal region of the handle 110. A needle cannula 130 is held within the handle 110 and a guidewire, which slides through the lumen defined by the needle cannula 130, is also held within the handle 110. The needle cannula 130 can be anchored within the handle 110 by an interference fit within an inner channel defined by the handle 110, by an adhesive, by a threaded connection, or the like. In some embodiments, the needle cannula 130 can be, for example, a 24 gauge needle.

A needle safety clip 134 is placed around the outer surface of the needle cannula 130 to cover the sharp needle tip 131 following separation of the insertion group 104 from the catheter group 102. A needle guard 136 covers the portion of the needle cannula 130 extending from the handle 110 before initial use of the catheter insertion device 100. A first actuator, such as a slider 138, is connected to the top of the handle 110 and to the guidewire 132 and slides the guidewire 132 relative to the handle 110 in both proximal and distal directions. In some embodiments, the guidewire 132 can be a spring wire guide, such as a coiled or a coil-less spring wire guide. The length of the guidewire 132 is selected such that, before the slider 138 is actuated, the distal end of the guidewire does not extend beyond the sharp needle tip 131 of the needle cannula 130.

In some embodiments, the guidewire 132 can have an outer diameter that is substantially uniform and less than or equal to 0.010 inches (0.0254 centimeters). Preferably, the guidewire 132 has an outer diameter that is less than or equal to 0.010 inches when the needle cannula 130 is a 24 GA needle and the elongated catheter 106 is a 22 GA catheter, so that the guidewire 132 can fit within the lumen defined by the 22 GA catheter. In other embodiments, the guidewire 132 can have a varying diameter that narrows distally, such that the diameter of the guidewire 132 is the smallest at a distal end of the guidewire 132. In some embodiments the guidewire 132 can be made of, for example, a metal, such as a metal alloy. For example, the guidewire 132 can be made of an alloy of nickel and titanium. In some embodiments, the guidewire 132 can be coated with polysulfones, polyfluorocarbons, polyolefins, polyesters, polyurethanes, blends and/or copolymers.

A second actuator, such as a release 140, is also connected to the handle 110 and to the catheter group 102 and slides the catheter group 102 relative to the handle 110 in a distal direction. The release 140 includes a proximal arm 174 having an enlarged proximal end 141. A needle support 142 is attached to a proximal region of the handle 110 and swings upward and downward relative to the handle 110 rotationally coupled to the top arm 127. The needle support 142 includes two parallel walls 143 separated by a distance slightly greater than the outer diameter of the elongated catheter 106 in which the needle cannula 130 passes to stabilize lateral movement of the needle cannula 130 during insertion of the needle in the vasculature of the patient. This stabilization is especially important for insertion of the needle relatively deep in the tissue of the patient, such as within an organ of the patient. The needle support 142 also includes a top portion 147 that abuts the bottom surface of the slider 138 before the slider 138 is slid proximally to prevent swinging of the release 140 while the catheter insertion device 100 is being inserted in the vasculature of the patient.

Referring to FIG. 3C, a perspective view of an assembled insertion group 104 of the catheter insertion device 100 having another implementation of the needle guard 137 is illustrated. The needle guard 137 includes an open channel 260 defined by two parallel side walls 262. A bottom longitudinal feature 264 and a top longitudinal feature 266 between the parallel side walls 262 secure around the needle cannula 130. As such, the bottom longitudinal feature 264 and the top longitudinal feature 266 are spaced apart by a distance slightly greater than the outer diameter of the needle cannula 130. The needle guard 137 also includes a tab 268 at the proximal end of the needle guard 137 to allow the practitioner to initially lift the needle guard 137 out of contact with the slider 138 and then push the needle guard 137 distally until the proximal ends of the bottom longitudinal feature 264 and the top longitudinal feature 266 are distal of the sharp needle tip 131. At this point, the needle guard 137 disengages from the insertion group 104 and can be removed to expose the sharp needle tip 131.

Figure 4:
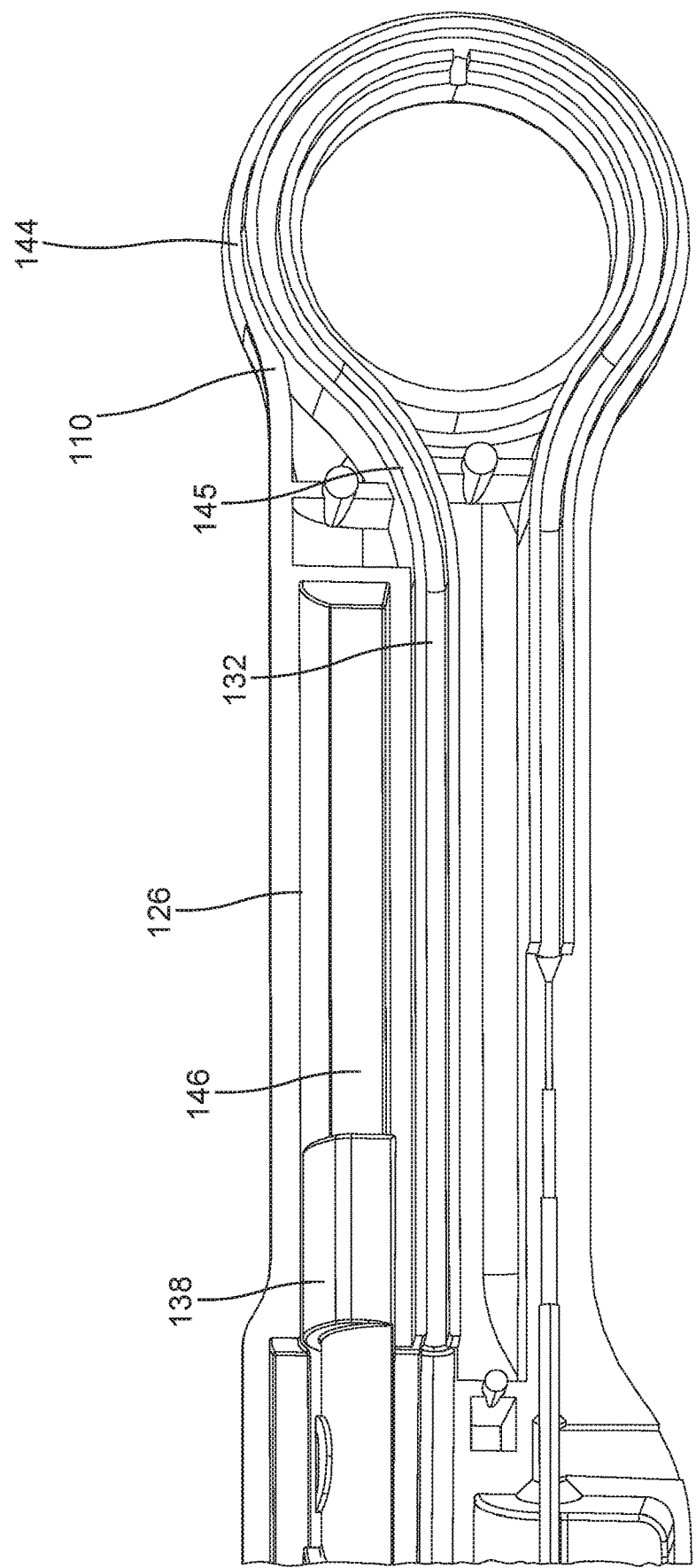
FIG. 4 illustrates a side view of a right housing of an assembled catheter insertion device.

Referring to FIG. 4, a side view of the right housing 126 including the slider 138 and the guidewire 132 is illustrated. The handle 110 includes a looped proximal end 144 through which the guidewire 132 passes. In particular, the guidewire 132 passes through the channel 145 defined by the handle 110. The diameter of the channel 145 is slightly greater than the diameter of the guidewire 132 so that the guidewire 132 stably passes through the channel 145. The slider 138 can be slid by a finger, such as the index finger in overhand operation or the thumb in underhand operation, of a practitioner proximally and distally within a chamber 146 defined by the handle 110. The chamber 146 is sized to be slightly larger than the slider 138 to stabilize the movement of the slider 138 within the chamber 146.

Due to the looping of the guidewire 132 within the looped proximal end 144, proximal movement of the slider 138 translates into distal movement of the distal tip of the guidewire 132 and vice versa. The looping of the guidewire 132, as opposed to a linear geometry, also enables one-handed operation of the catheter insertion device 100 while maintaining continuous grip of the gripping features 148 of the handle 110. In addition, the looping of the guidewire 132 reduces the likelihood of piercing the vasculature of the patient during advancement of the guidewire 132 due to the force of the practitioner being indirectly applied to the guidewire 132.

Figure 5:
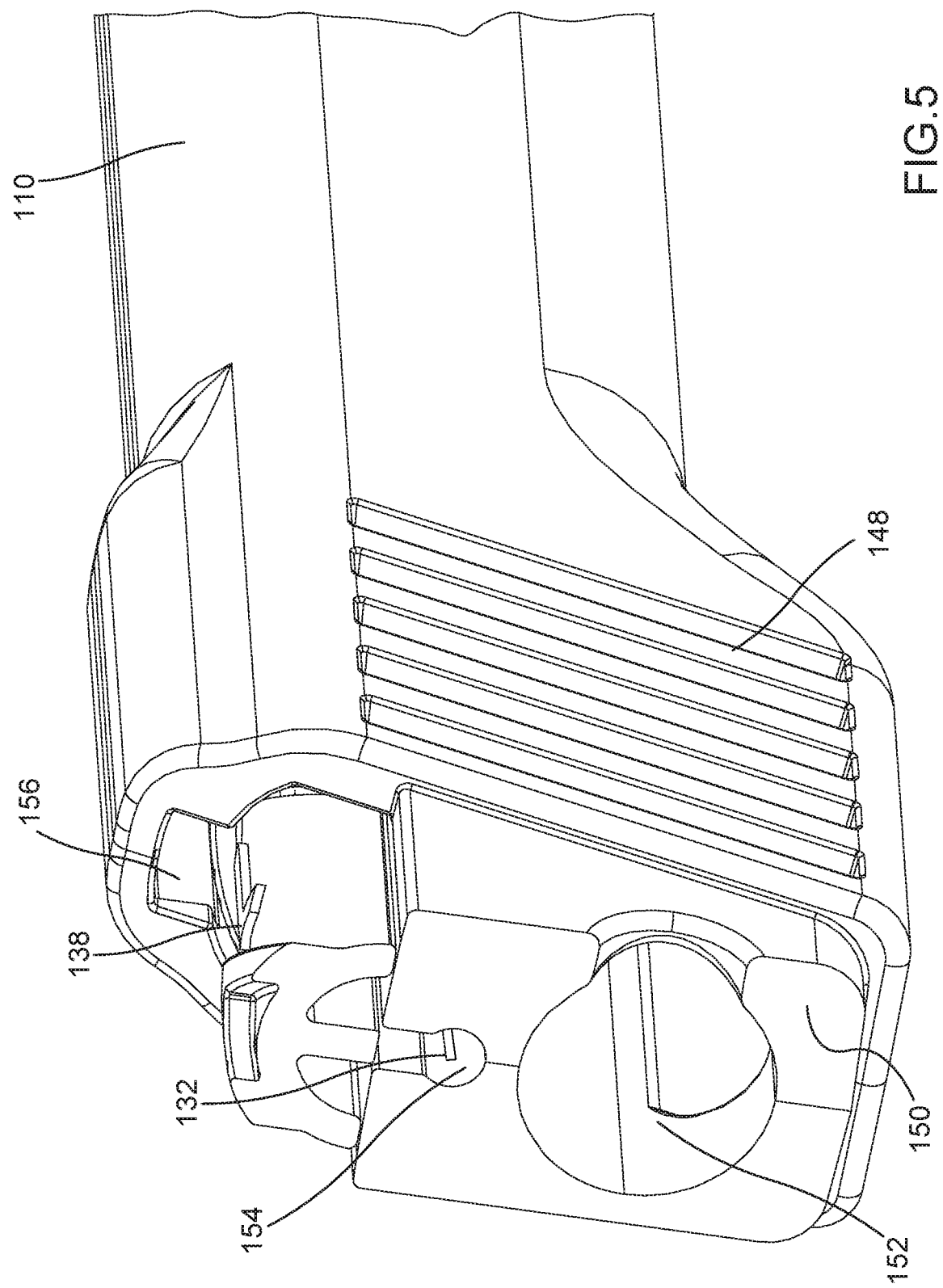
FIG. 5 illustrates a cross-sectional view of a handle of an assembled catheter insertion device.

Referring to FIG. 5, a cross-section view of the assembled handle 110 with the guidewire 132 and the slider 138 is illustrated. The handle 110 includes gripping features 148 that help the practitioner grip the handle 110 of the catheter insertion device 100. A right-handed practitioner can, for example, grip the gripping feature 148 on the left housing 128 using his thumb and grip the gripping feature 148 on the right housing using his middle finger or left-handed practitioner can, for example, grip the gripping feature 148 on the left housing 128 using his middle finger and grip the gripping feature 148 on the right housing using his thumb. The handle 110 can be gripped by the practitioner overhand or underhand using the same fingers. Although depressed lines are shown as the gripping features 148, any gripping feature can be formed on the outer surface of the handle 110. For example, raised lines can be formed in place of the depressed lines, a textured surface can be formed, a plurality of bumps can be formed, or a different material, such as rubber, can be formed over the region of the handle 110 corresponding to the gripping features 148.

Three openings are defined by the front face 150 of the handle 110. The bottom opening 152 is sized to receive the rigid hub cap 124 of the catheter group 102. In particular, the diameter of the bottom opening 152 is slightly greater than the diameter of the rigid hub cap 124. The middle opening 154 is sized to receive the guidewire 132 and the needle cannula 130, and the top opening 156 is sized to receive the slider 138 and the proximal arm of the release 140 (not shown). The top opening 156 includes a wider bottom region that receives the slider 138 and a narrower top region that receives the proximal arm of the release 140. The bottom opening 152 and the middle opening 154 are separated by a portion of the handle 110, whereas the middle opening 154 and the top opening 156 are not separated to allow a bottom arm 158 (not shown) of the slider 138 to slide within middle opening 154, as explained in greater detail below.

In particular, referring to FIG. 6, a transparent side view of a portion of the slider 138 is illustrated. The slider 138 includes a bottom arm 158 extending from the bottom of the slider 138 in a direction perpendicular to the longitudinal axis of the slider 138. The bottom arm 158 includes a through hole 160 that receives the proximal end 133 of the guidewire 132. The through hole 160 has an internal diameter that is slightly larger than the outer diameter of the guidewire 132 but slightly smaller than the diameter of the ball 162 formed at the end of the guidewire 132. The guidewire 132 is therefore secured within the through hole 160 by a interference fit. The through hole 160 does not extend along the entirety of the length of the bottom arm 158, such that the distal end of the through hole 160 is closed. Although the ball 162 is secured within the through hole 160 by a interference fit, in some implementations, the ball 162 can be secured by an adhesive, by a threaded connection, or the like.

Due to the interference fit between the through hole 160 and the guidewire 132, as the slider 138 is moved in a longitudinal direction for a given distance, the guidewire will also move in the opposite direction for the same distance and vice versa. The slider 138 includes one or more grips 164 that allow a finger, such as the index finger in an overhand operation or the thumb in an underhand operation, of the practitioner to predictably actuate the slider 138 in either a distal or proximal direction. In some embodiments, as shown in FIG. 6, the grips 164 can be shaped like arrows that point in the proximal direction. Adjacent to each grip 164 can be an indicator 166, such as a number, that indicates a relative extension of the guidewire 132 distally from the sharp needle tip 131.

Referring to FIG. 7A, the left side of the release 140 includes a notch 168 that receives the side port 121. The release 140 is sized to be received from around the bottom arm 129 to the slider 138. The notch 168 is sized to be slightly larger than the diameter of the side port 121 to stably secure the side port 121. When the practitioner actuates the release 140 in a distal direction using, for example, his index finger, the catheter group 102 is also actuated in the distal direction by the same distance through the interface between the notch 168 and the side port 121.

Figure 7B:
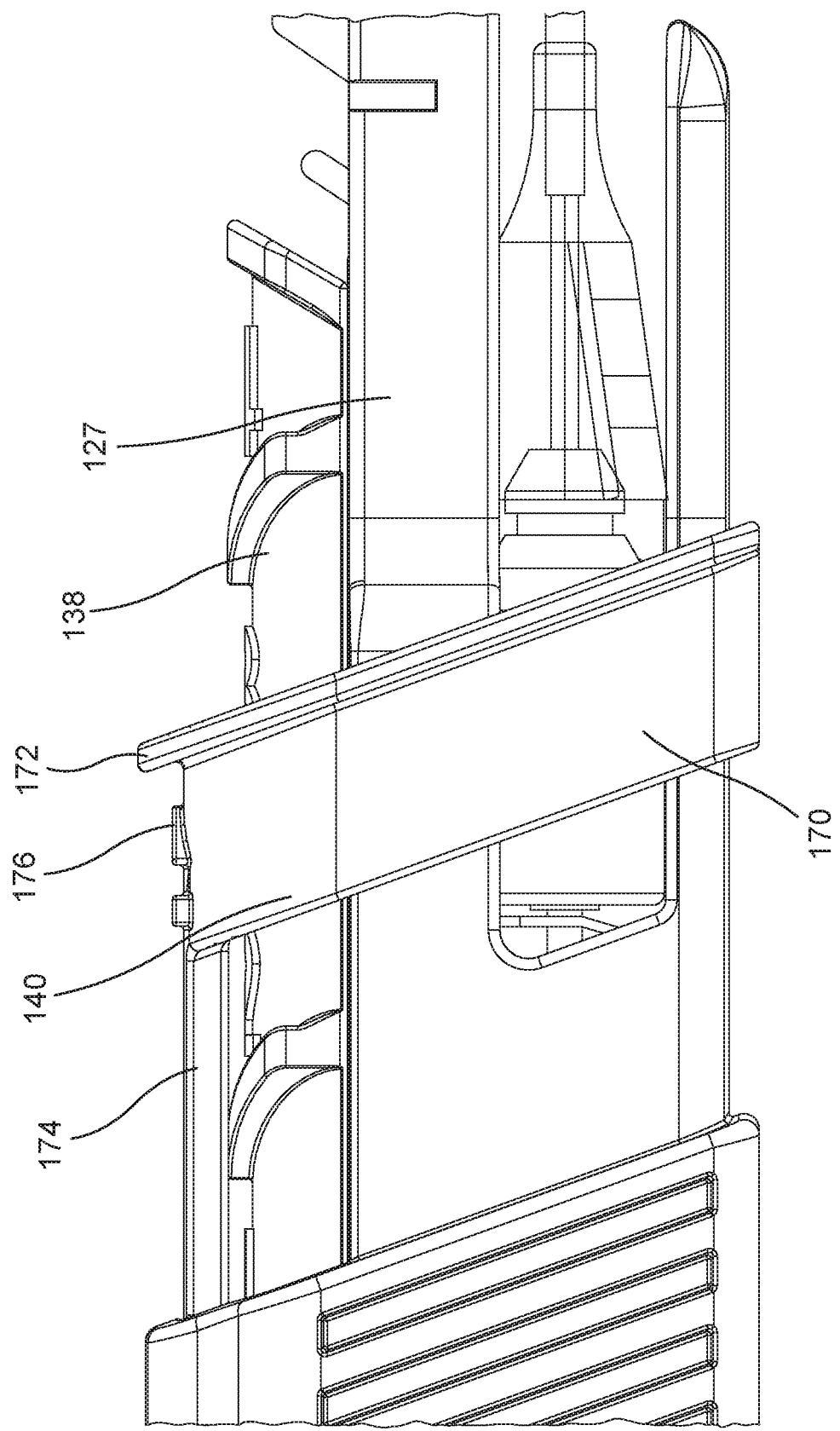
FIG. 7B illustrates the right side of the release of the insertion group of the catheter insertion device.

Referring to FIG. 7B, the right side of the release 140 includes a continuous side wall 170. If the practitioner's finger were to push down onto the slider 138 or top arm 127 of the handle 110 while the needle cannula 130 is still in the vasculature of the patient, the resulting downward movement of the needle cannula 130 may cause damage to the vasculature of the patient. As such, to help prevent the practitioner's finger from slipping past the distal end of the release 140, the release 140 includes a distal lip 172 that extends radially outward from the release 140.

The release 140 also includes a proximal arm 174 having an enlarged proximal end 141 (not shown). The proximal arm 174 slides within the top opening 156 of the handle 110. The enlarged proximal end of the release 140 is dimensioned to be larger than the top opening 156 so that distal movement of the release 140 is limited to the length of the proximal arm 174 and so that the release 140 does not separate from the handle 110. The release 140 can also include a grip 176 that allow a finger, such as the index finger in an overhand operation or the thumb in an underhand operation, of the practitioner to predictably actuate the release 140 in either a distal or proximal direction.

Figure 8A:
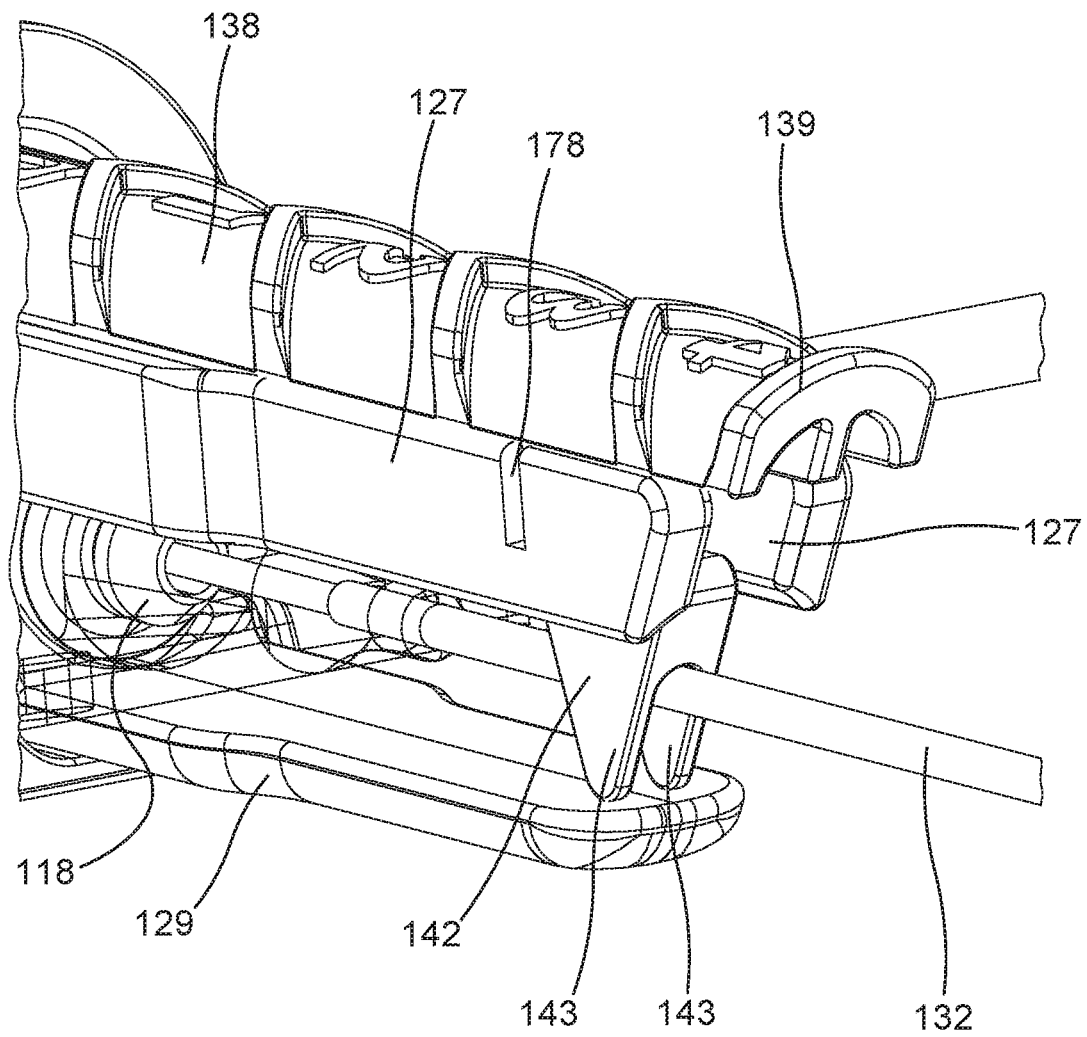
FIG. 8A illustrates a partially transparent perspective view of a region of the assembled catheter insertion device.

Referring to FIG. 8A, a partially transparent perspective view of a region of the assembled catheter insertion device 100 is illustrated. The bottom arms 129 of the right housing 126 and the left housing 128 abut against one another to support the weight of the juncture hub 118. The top arms 127 of the right housing 126 and the left housing 128 are spaced apart by a distance slightly greater than the width of the needle support 142 to allow the needle support 142 to swing upwards during removal of the catheter group 102. The needle support 142 includes two parallel walls 143 that are perpendicular to the plane of the top surface of the bottom arms 129. As explained above, the parallel walls 143 are spaced apart by a distance slightly greater than the outer diameter of the elongated catheter 106 to stabilize the needle cannula 130 during insertion into the vasculature of the patient. Both top arms 127 also include a groove 178 that received a corresponding tongue of the needle guard 136. The tongue and groove connection stably secures the needle guard 136 to the handle 110 before use of the catheter insertion device 100.

Figure 8B:
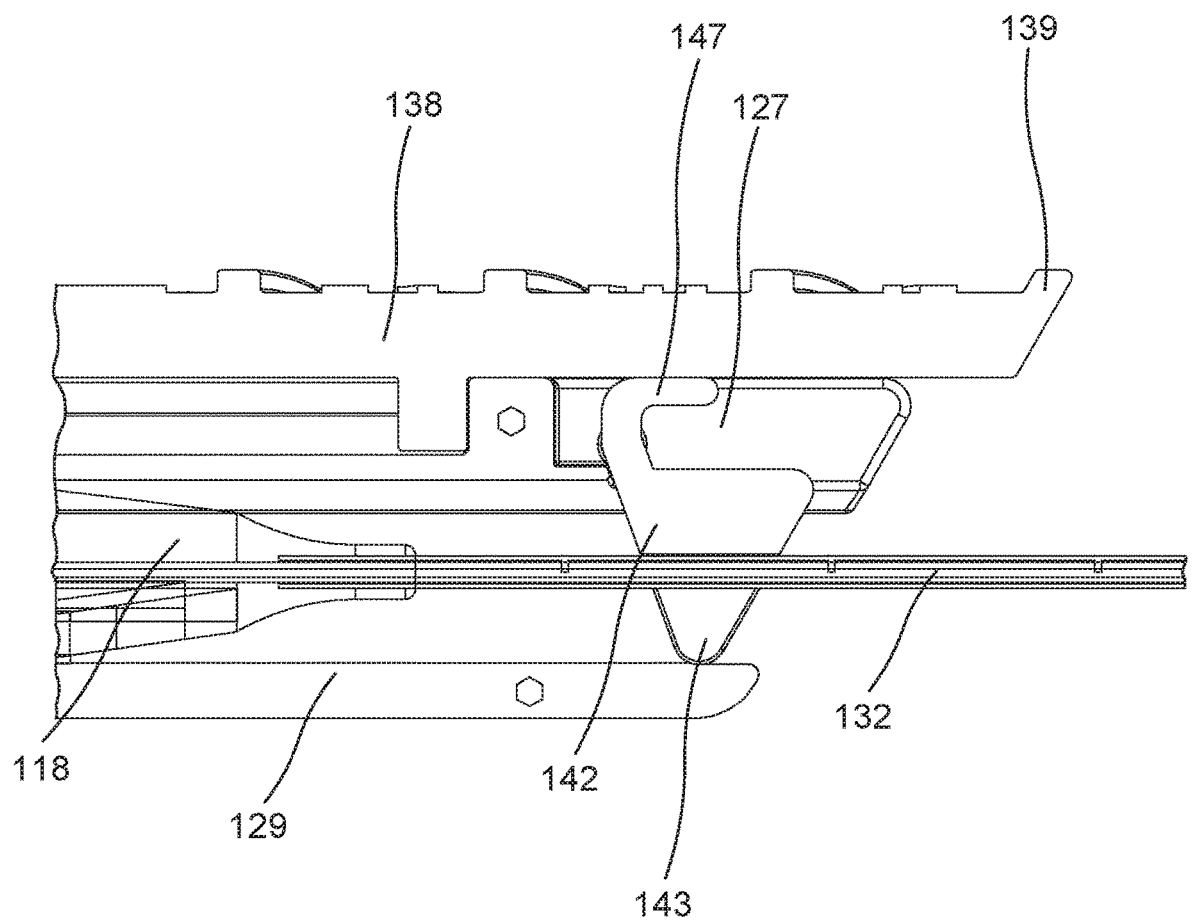
FIG. 8B illustrates a partial cross-sectional view of the region of the assembled catheter insertion device along the center longitudinal plane of the handle.

Before the practitioner slides the slider 138 proximally, the distal end 139 of the slider 138 extends beyond the distal end of the top arm 127 and, as such, extends distally beyond the needle support 142. As shown in FIG. 8B, which illustrates a partial cross-sectional view of the region of the assembled catheter insertion device 100 along the center longitudinal plane of the handle 110, the bottom surface of the slider 138 abuts against the top portion 147 before the slider 138 is slid proximally to prevent swinging of the release 140 while the catheter insertion device 100 is being inserted in the vasculature of the patient.

Figure 8C:
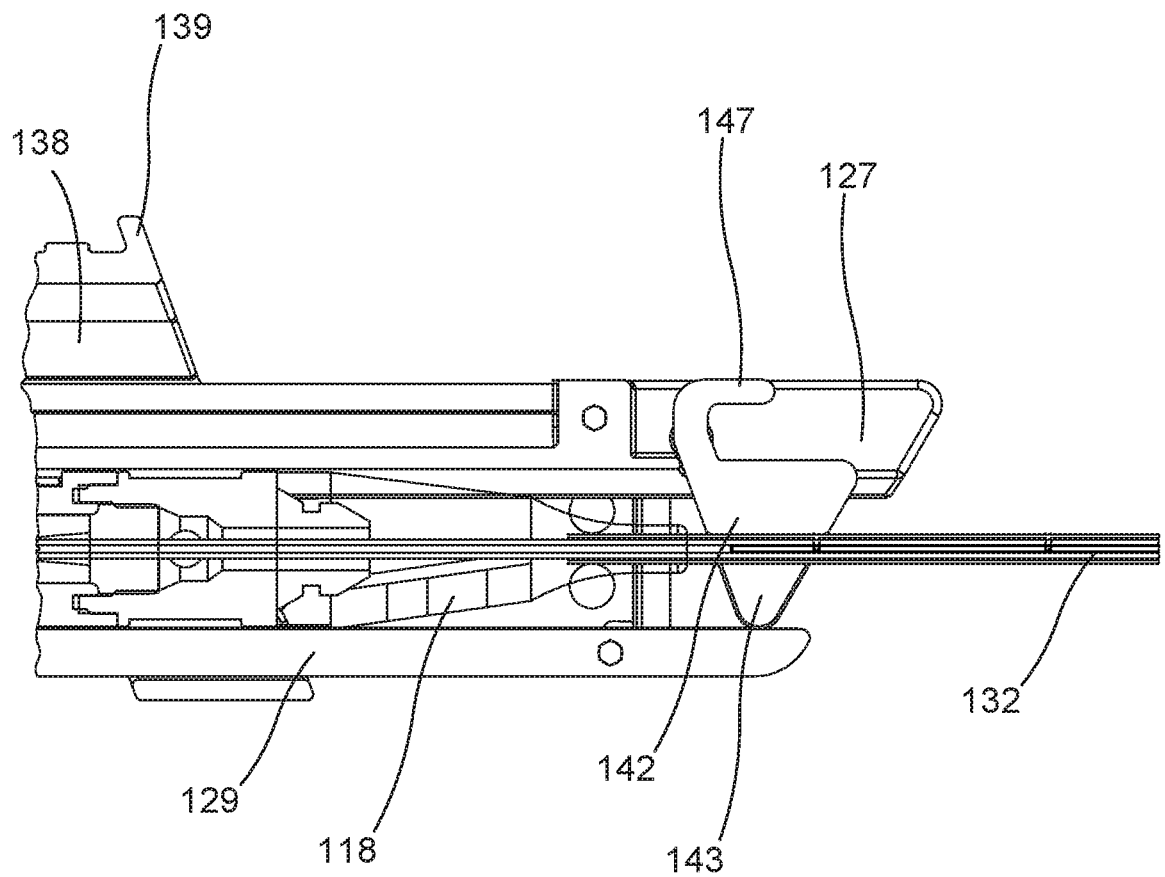
FIG. 8C illustrates a partial cross-sectional view of the region of the assembled catheter insertion device along the center longitudinal plane of the handle following actuation of the slider by the practitioner.

FIG. 8C illustrates a partial cross-sectional view of the region of the assembled catheter insertion device 100 along the center longitudinal plane of the handle 110 following actuation of the slider 138 by the practitioner. As shown in FIG. 8C, the distal end 139 of the slider 138 is proximal of the needle support 142 so that the top portion 147 no longer abuts the bottom surface of the slider 138 and is free to swing upwards as the catheter group 102 is separated from the insertion group 104.

Figure 8D:
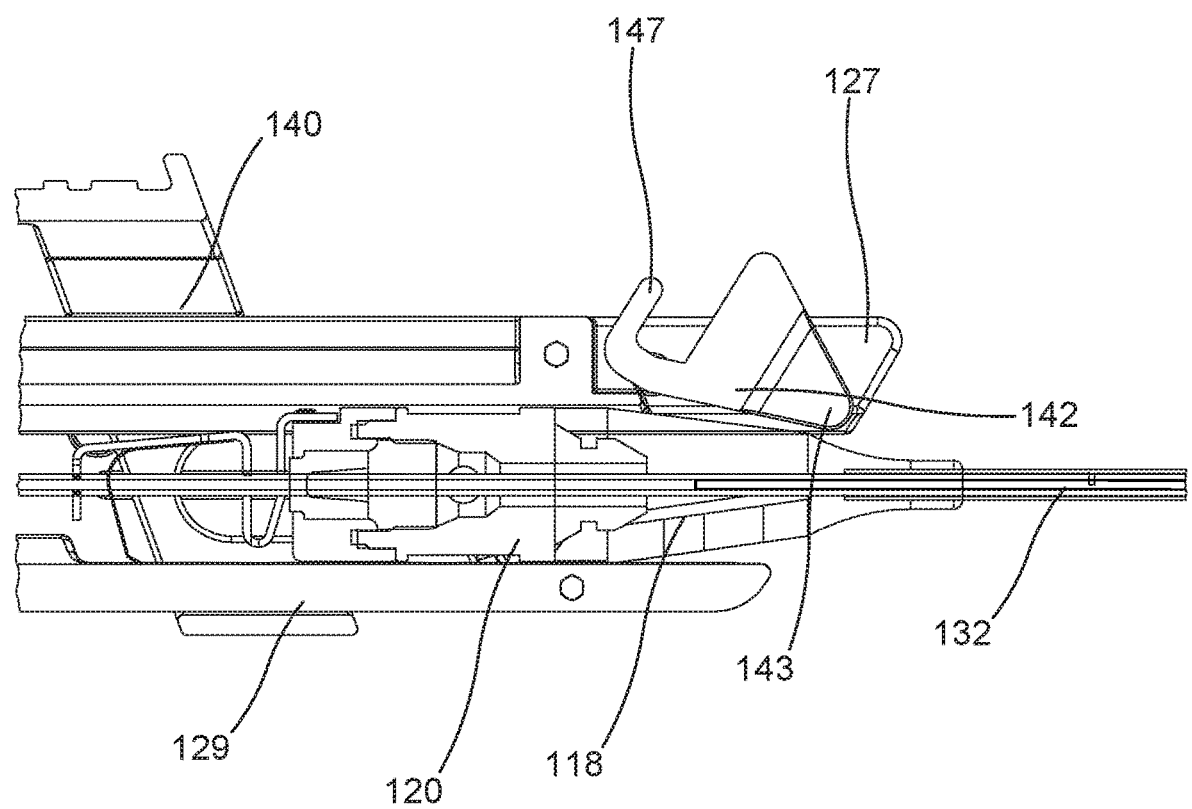
FIG. 8D illustrates a partial cross-sectional view of the region of the assembled catheter insertion device along the center longitudinal plane of the handle following actuation of the release by the practitioner.

FIG. 8D illustrates a partial cross-sectional view of the region of the assembled catheter insertion device 100 along the center longitudinal plane of the handle 110 following actuation of the release 140 by the practitioner. As shown in FIG. 8D, the release 140 pushes the rigid hub 120 distally so that the distal end of the juncture hub 118 extends distally beyond the needle support 142. As the juncture hub 118 initially abuts and distally moves past the needle support 142, the needle support 142 swings upward to provide clearance for full deployment of the catheter group 102.

Figure 9A:
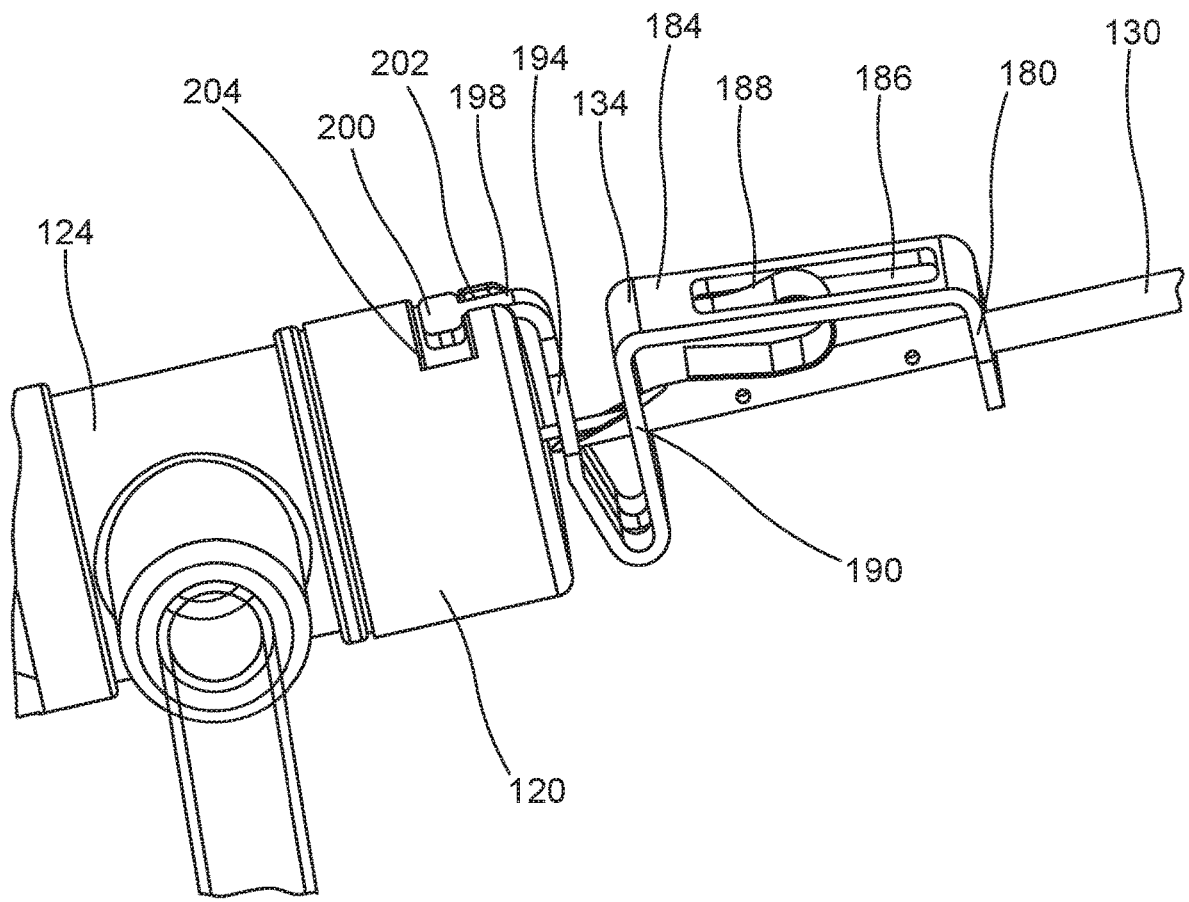
FIG. 9A illustrates a perspective view of a needle safety clip mounted to a catheter hub of the catheter group of the catheter insertion device.
Figure 9B:
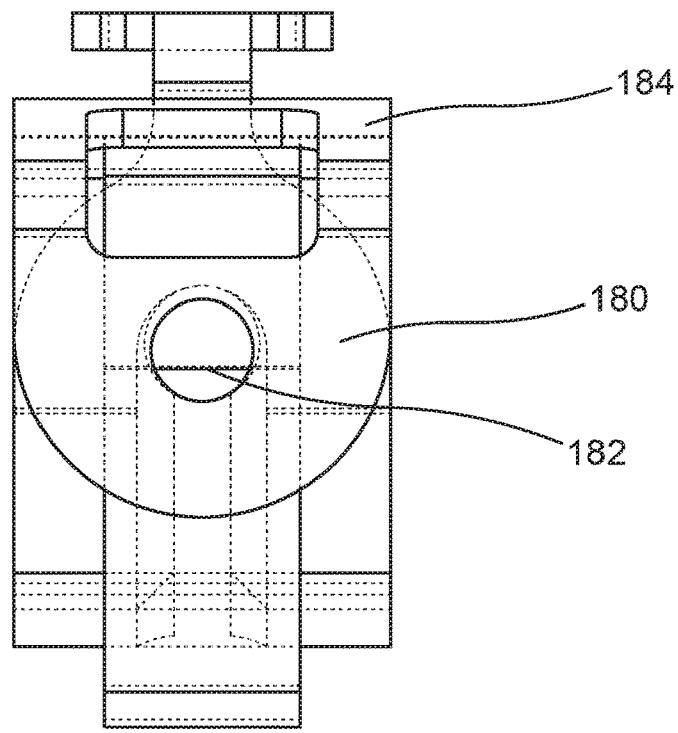
FIG. 9B illustrates a rear view of the needle safety clip.
Figure 9C:
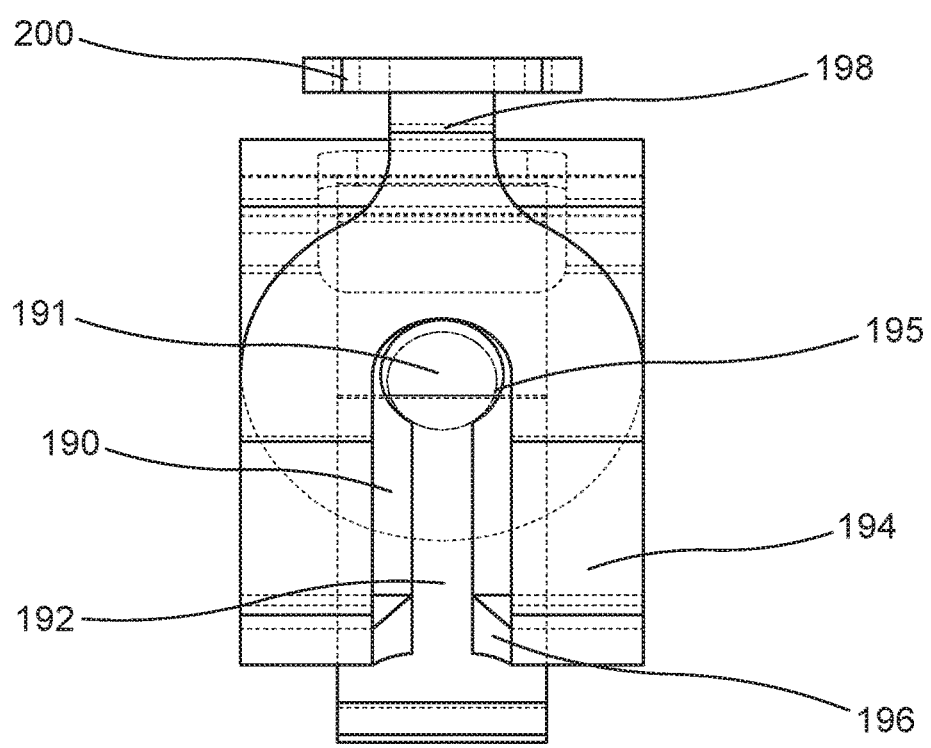
FIG. 9C illustrates a front view of the needle safety clip.
Figure 9D:
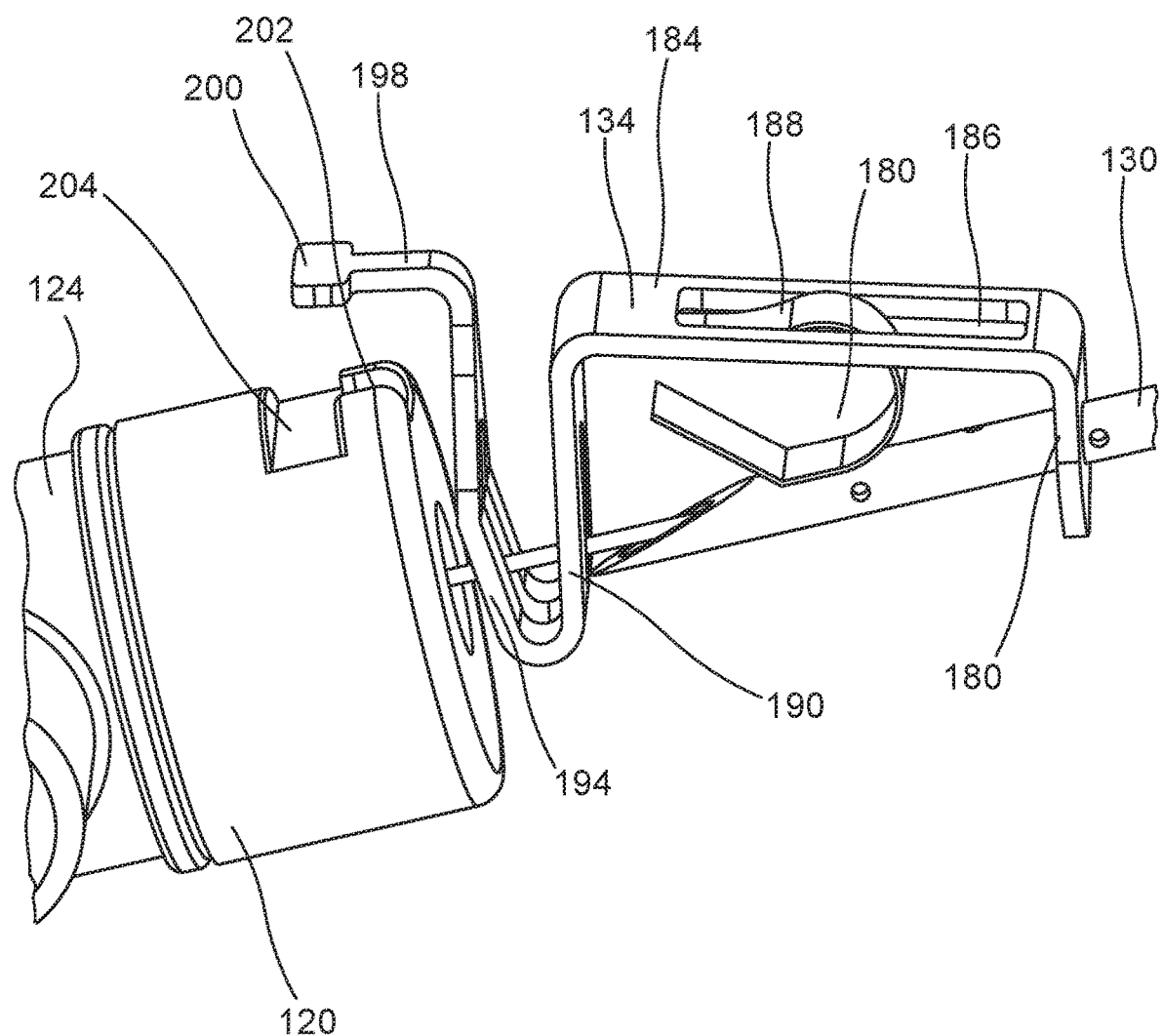
FIG. 9D illustrates a perspective view of the needle safety clip released from the catheter hub of the catheter group of the catheter insertion device.

Referring to FIG. 9A, a perspective view of the needle safety clip 134 mounted to the rigid hub 120 is illustrated. Referring to FIG. 9B, a rear view of the needle safety clip 134 is illustrated. Referring to FIG. 9C, a front view of the needle safety clip 134 is illustrated. The needle safety clip 134 includes a proximal wall 180 that includes a round aperture 182 having a diameter slightly greater than the outer diameter of the needle cannula 130. In some implementations, the round aperture 182 can have a sharp inner surface to grip the outer surface of the needle cannula 130 when the needle cannula 130 is at an angle with respect to the central axis of the round aperture 182. In other words, the sharp inner surface of the round aperture 182 digs into the outer surface of the needle cannula 130 when the needle cannula 130 is tilted with respect to the needle safety clip 134, as shown in FIG. 9D, to prevent movement of the needle cannula 130 with respect to the needle safety clip 134.

Referring back to FIG. 9A, a top wall 184 extends distally of the proximal wall 180 and defines a top opening 186. The top opening 186 allows the spring arm 188 to extend partially above the top wall 184 in its compressed state, as shown in FIG. 9A. The spring arm 188 is illustrated to be C-shaped. However, the spring arm 188 can be designed to have other shapes that are resilient and can be shaped to be, for example, stepped, blocked, jagged, or amorphous. The top distal portion of the spring arm 188 is connected to the distal bottom surface of the top wall 184 to secure the spring arm 188 to the rest of the needle safety clip 134. The spring arm 188 can be made of any flexible material, such as, for example, plastic, stainless steel, aluminum or titanium. The spring arm 188 can be made of the same material as the rest of the needle safety clip 134 or made of a different material having the desired characteristics.

A first distal wall 190 extends downward from the distal end of the top wall 184 and defines a first distal channel. A second distal wall 194 curves upward from the first distal wall 190 and defines a second distal channel. A narrow tab 198 extends distally from the distal end of the second distal wall 194 and a broad tab 200 extends distally from the narrow tab 198. The narrow tab 198 is received within a narrow recess 202 at the top of the rigid hub cap 124 and the broad tab 200 is received within a broad recess 204 at the top of the rigid hub cap 124 to mount the needle safety clip 134 to the rigid hub cap 124. When the needle safety clip 134 is mounted to the rigid hub cap 124, the narrow tab 198 prevents lateral movement of the needle safety clip 134 while broad tab 200 prevents longitudinal movement of the needle safety clip 134.

Referring back to FIG. 9C, the first distal wall 190 defines a channel having a round top region 191 and a rectangular bottom region 192. The diameter of the round top region 191 is slightly larger than the outer diameter of the needle cannula 130 to allow the needle cannula 130 to slide through the round top region 191 with low friction and to prevent lateral movement of the needle cannula 130. The rectangular bottom region 192 has a width that is less than the outer diameter of the needle cannula 130 to block the needle cannula 130 from being able to extend distally past the second distal wall 194, as explained in greater detail below. The second distal wall 194 also includes a round top region 195 that has a diameter that is greater than the outer diameter of the needle cannula 130 and a rectangular bottom region 196. The width of the rectangular bottom region 196 can be equal to the diameter of the round top region 195 to allow the needle cannula 130 to move downward relative to the needle safety clip 134 under force of the spring arm 188.

Referring to FIG. 9D, a perspective view of the needle safety clip 134 released from the rigid hub 120 is illustrated. After the needle cannula 130 is withdrawn from the rigid hub 120, it passes proximally through the round top region 195 of the second distal wall 194 and then through the round top region 191 of the first distal wall 190. Once the round top region 191 does not stabilize the needle cannula 130, the needle cannula 130 is free to tilt relative to the needle safety clip 134. The spring arm 188 then decompresses, as shown in FIG. 9D, to push the needle safety clip 134 upward. Because the needle cannula 130 is still within the round aperture 182, it is gripped by the sharp inner edges of the round aperture 182, which prevents longitudinal movement of the needle cannula 130 with respect to the needle safety clip 134. As such, the first distal wall 190 and the second distal wall 194 cover the sharp needle tip 131 and protect the practitioner from potential needle pricks.

Figure 9E:
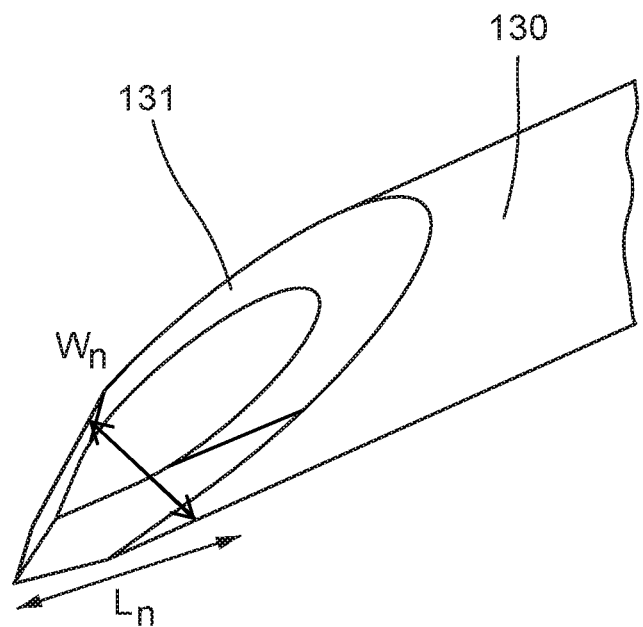
FIG. 9E illustrates a perspective view of a sharp needle tip of the needle.
Figure 9F:
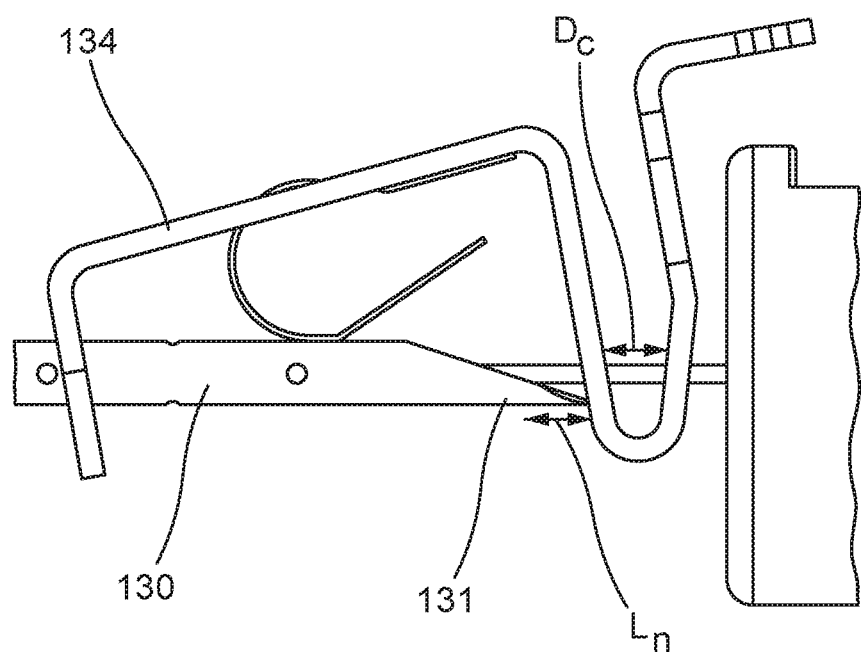
FIG. 9F illustrates the sharp needle tip being withdrawn from the needle safety clip.

Referring to FIG. 9E, a perspective view of the sharp needle tip 131 of the needle cannula 130 is illustrated. As shown in FIG. 9E, the sharp needle tip 131 can have a lancet tip or, in other implementations, the sharp needle tip 131 can be formed by back grinding. The sharp needle tip 131 tapers in the distal direction such that the width $W_n$ of the sharp needle tip 131 at a plane along the sharp needle tip 131 is equal to the width of the rectangular bottom region 192. As such, the needle cannula 130 cannot extend distally past the first distal wall 190 beyond that plane where the sharp needle tip 131 has the width $W_n$ when the needle safety clip 134 is released from the rigid hub 120 because the needle cannula 130 is wider than the rectangular bottom region 192 proximal of that plane. However, the length $L_n$ can still extend distally beyond the first distal wall 190 because the needle cannula 130 is thinner than the rectangular bottom region 192 distal of that plane. Therefore, as shown in FIG. 9F, to prevent exposure of the sharp needle tip 131 beyond the second distal wall 194, the needle safety clip 134 is designed so that the distance $D_c$ between the first distal wall 190 and the second distal wall 194 in the axis aligned with the longitudinal axis of the needle cannula 130 is greater than the length $L_n$.

Figure 10A:
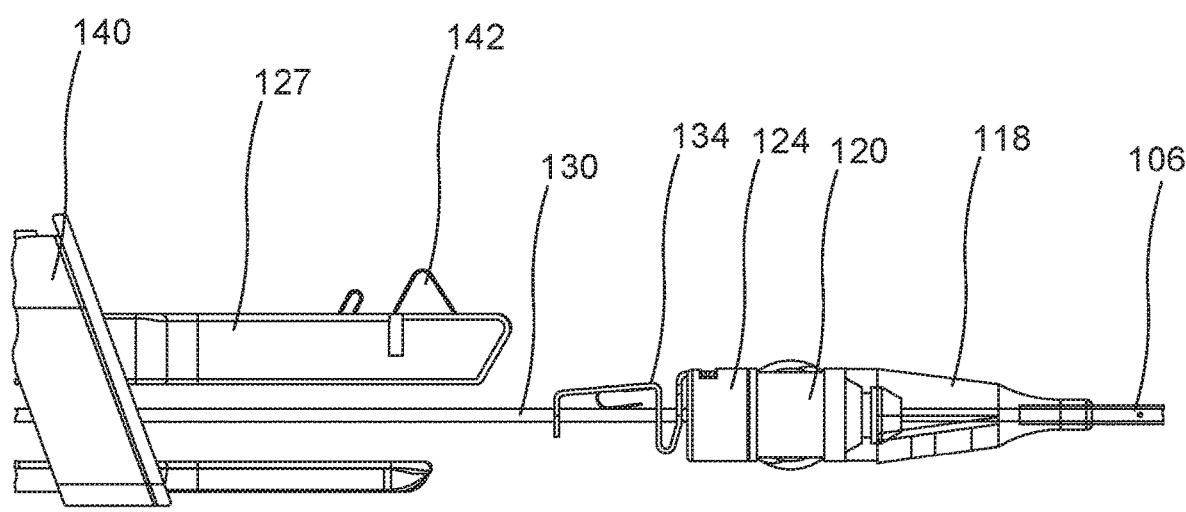
FIG. 10A illustrates the insertion group being pulled proximally such that the catheter group is distal of the handle.
Figure 10B:
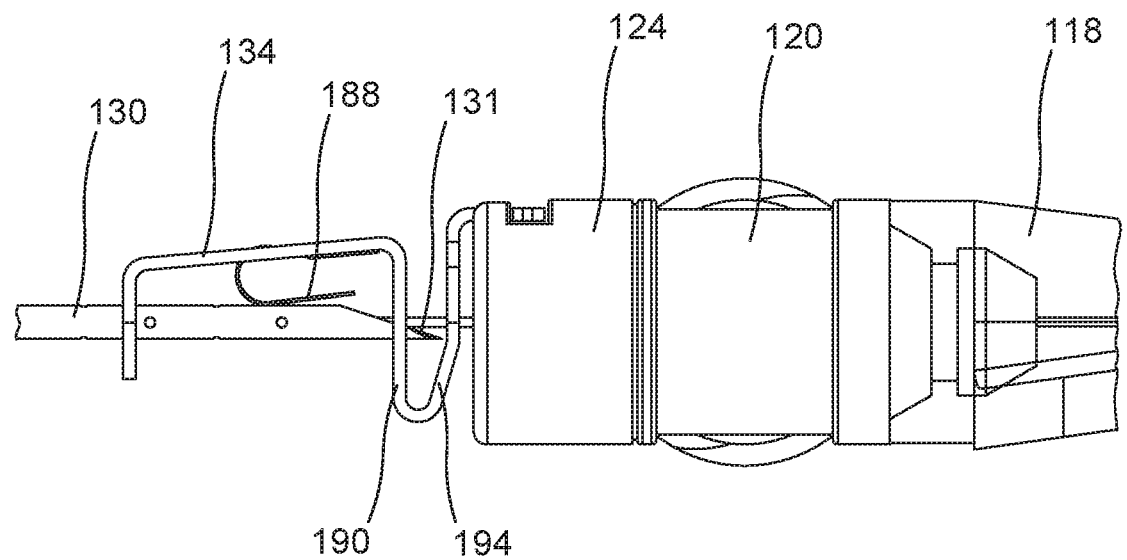
FIG. 10B illustrates the insertion group being pulled proximally to the point where the sharp needle tip of the needle is between two distal walls of the needle safety clip.
Figure 10C:
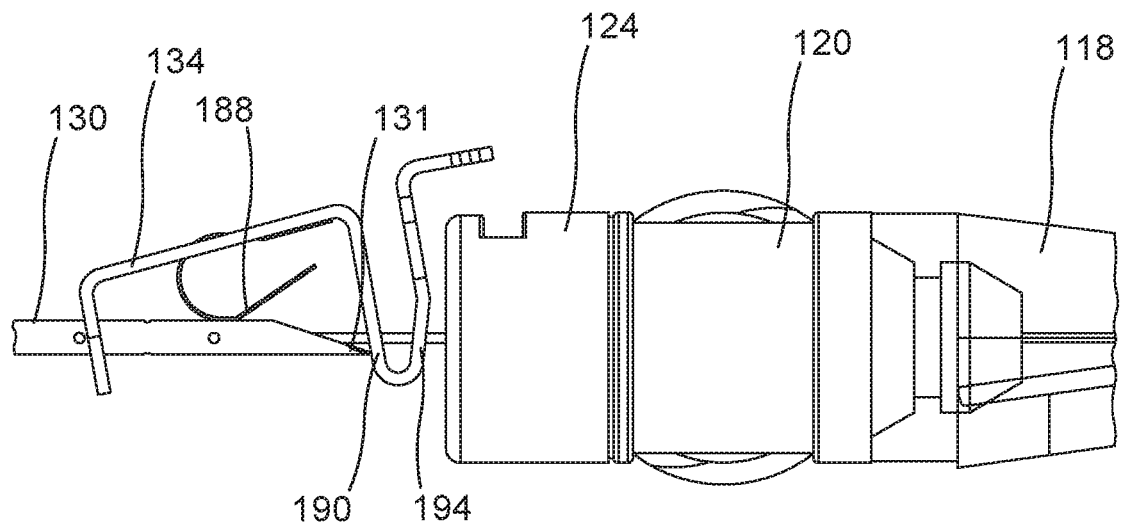
FIG. 10C illustrates the insertion group being pulled proximally to the point where the sharp needle tip of the needle is proximal of both the two distal walls of the needle safety clip and is tilted relative to the needle safety clip.

Referring to FIGS. 10A-C, partially transparent side views of the catheter insertion device 100 during separation of the catheter group 102 are illustrated. As explained above in connection with FIG. 8D, the release 140 is initially slid distally to allow the needle support 142 to swing upwards. The practitioner then uses the hand that is not grasping the handle 110 to stabilize the catheter group 102. For example, the practitioner can use his non-dominant hand to grasp the juncture hub 118 and/or the rigid hub 120 to stabilize the rigid hub 120 at a constant position within the vasculature of the patient. The practitioner can then pull the insertion group 104 proximally to remove the needle cannula 130 from the catheter group 102.

As shown in FIG. 10A, the insertion group 104 is pulled proximally such that the catheter group 102 is distal of the distal end of the handle 110. At this point, the needle safety clip 134 is still mounted to the rigid hub cap 124, as explained above. As shown in FIG. 10B, the insertion group 104 is pulled proximally to the point where the sharp needle tip 131 of the needle cannula 130 is proximal of the second distal wall 194, but still distal of the first distal wall 190. As such, the plane where the sharp needle tip 131 has the width $W_n$ is still distal of the first distal wall 190 and the needle cannula 130 is stabilized within the round top region 191. As shown in FIG. 10C, the sharp needle tip 131 is proximal of the first distal wall 190 and, therefore, free to tilt relative to the needle safety clip 134. The spring arm 188 then decompresses to tilt the needle cannula 130 downward, so that the first distal wall 190 and/or the second distal wall 194 cover the sharp needle tip 131.

Figure 11A:
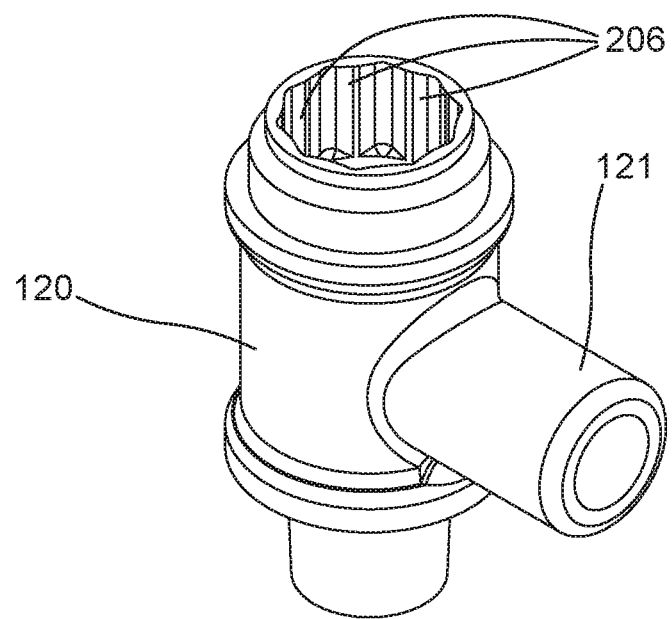
FIG. 11A illustrates a perspective view of a rigid hub of the catheter group of the catheter insertion device.

Referring to FIG. 11A, a perspective view of the rigid hub 120 is illustrated. The rigid hub 120 can include two or more compression ribs 206 protruding radially inward along an inner circumference of the proximal end of the rigid hub 120 to allow for oversizing of the valve 122. The compression ribs 206 grip the valve 122 within the rigid hub 120. The radial interference caused by the compression ribs 206 on the valve 122 acts to seal the puncture hole created by the needle cannula 130 with the valve 122 following separation of the catheter group 102 from the insertion group 104. The areas between the compression ribs 206 provide a region for the material of the valve 122 to displace when the valve 122 is compressed.

Figure 11B:
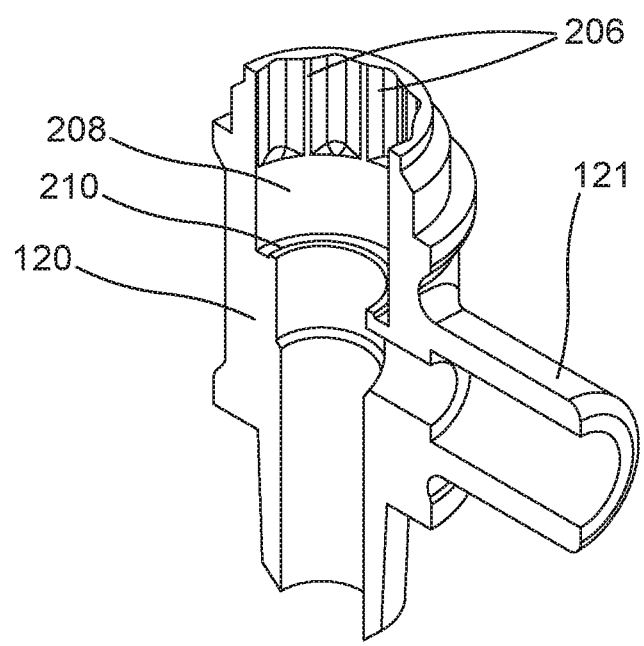
FIG. 11B illustrates a cross-sectional view of the rigid hub of the catheter group of the catheter insertion device.

Referring to FIG. 11B, a cross-sectional view of the rigid hub 120 taken along the plane defined by the diameter of the rigid hub 120 and the longitudinal axis of the side port 121 is illustrated. The smooth region 208 just distal of the compression ribs 206 has a diameter that is smaller than the diameter of the valve 122 to radially seal the valve 122 within the rigid hub 120. The annular flange 210 abuts against the flat distal face 214 of the valve 122 to prevent distal movement of the valve 122 when the needle cannula 130 applies distal pressure to the valve 122.

Figure 12A:
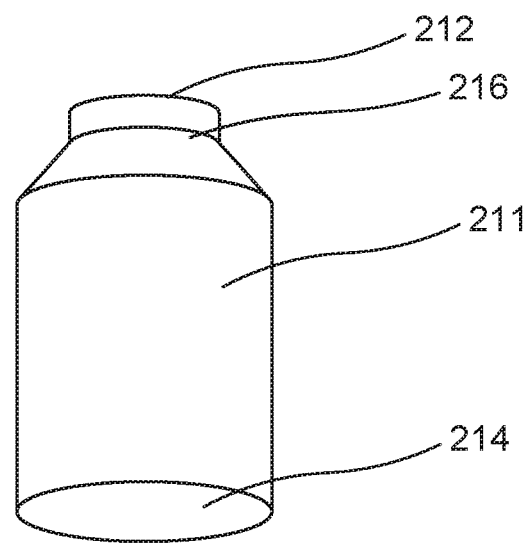
FIG. 12A illustrates a perspective view of a first implementation of a valve.

Referring to FIG. 12A, a perspective view of a first implementation of the valve 211 is illustrated. The valve 211 includes a flat proximal face 212 and a flat distal face 214. The valve 211 has a substantially uniform outer diameter in the regions that are received within the rigid hub 120 to allow for a compression fit within the rigid hub cap 124. The proximal region of the valve 211 has a wedged surface 216 that enlarges distally. The valve 221 is solid and made of a resilient material, such as, for example, silicon, rubber, polyisoprene, or the like.

Figure 12B:
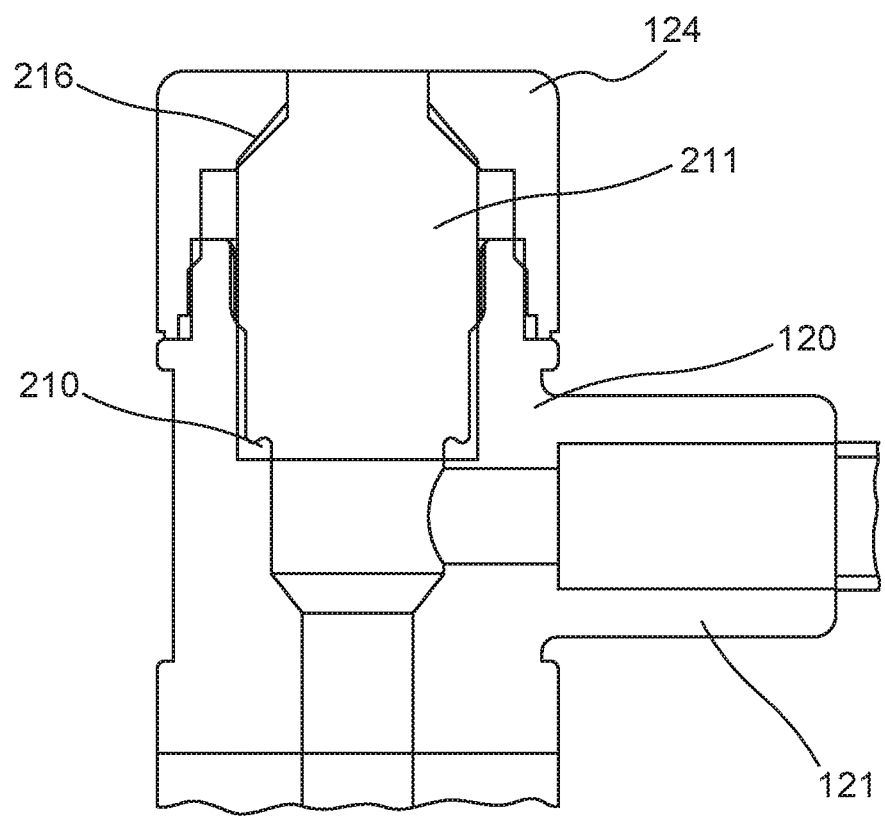
FIG. 12B illustrates a partial cross-sectional view of the first implementation of the valve within the catheter hub of the catheter group.

Referring to FIG. 12B, a partial cross-sectional view of the assembled rigid hub 120, valve 122, and rigid hub cap 124 taken along the plane defined by the diameter of the rigid hub 120 and the longitudinal axis of the side port 121 is illustrated. The wedged surface 216 of the valve 211 is compressed within the rigid hub cap 124 to force the valve material radially inward in response to pressure applied to the flat distal face 214. As shown in FIG. 12B, the flat distal face 214 is flush with the distal end of the rigid hub cap 124 to allow for complete evacuation of the inner volume of the rigid hub 120 when flushing the catheter insertion device 100.

Referring to FIG. 13A, a perspective view of a second implementation of the valve 218 is illustrated. The valve 218 is a two-part valve that includes a proximal part 220 and a distal part 222. Referring to FIG. 13B, the proximal part 220 has a flat proximal face 224 and a proximal region 228 having a reduced diameter. The proximal part 220 defines an inner cavity 230 that extends along a majority of the longitudinal axis of the proximal part 220. Relative to the valve 211, the inner cavity 230 reduces the surface area of the valve 218 that the needle cannula 130 must pass through, thereby reducing the force required to insert the needle cannula 130.

Referring to FIG. 13C, the distal part 222 is solid and includes a proximal region 232 of reduced diameter. The diameter of the proximal region 232 is slightly smaller than the diameter of the inner cavity at the distal end of the proximal part 220 to prevent lateral movement of the distal part 222 relative to the proximal part 220 when the valve 218 is assembled within the rigid hub 120 and the rigid hub cap 124. The distal part 222 also has a tapered distal region with a diameter that reduces distally. The valve 218 can be made of a resilient material, such as, for example, silicon, rubber, polyisoprene, or the like.

Figure 13D:
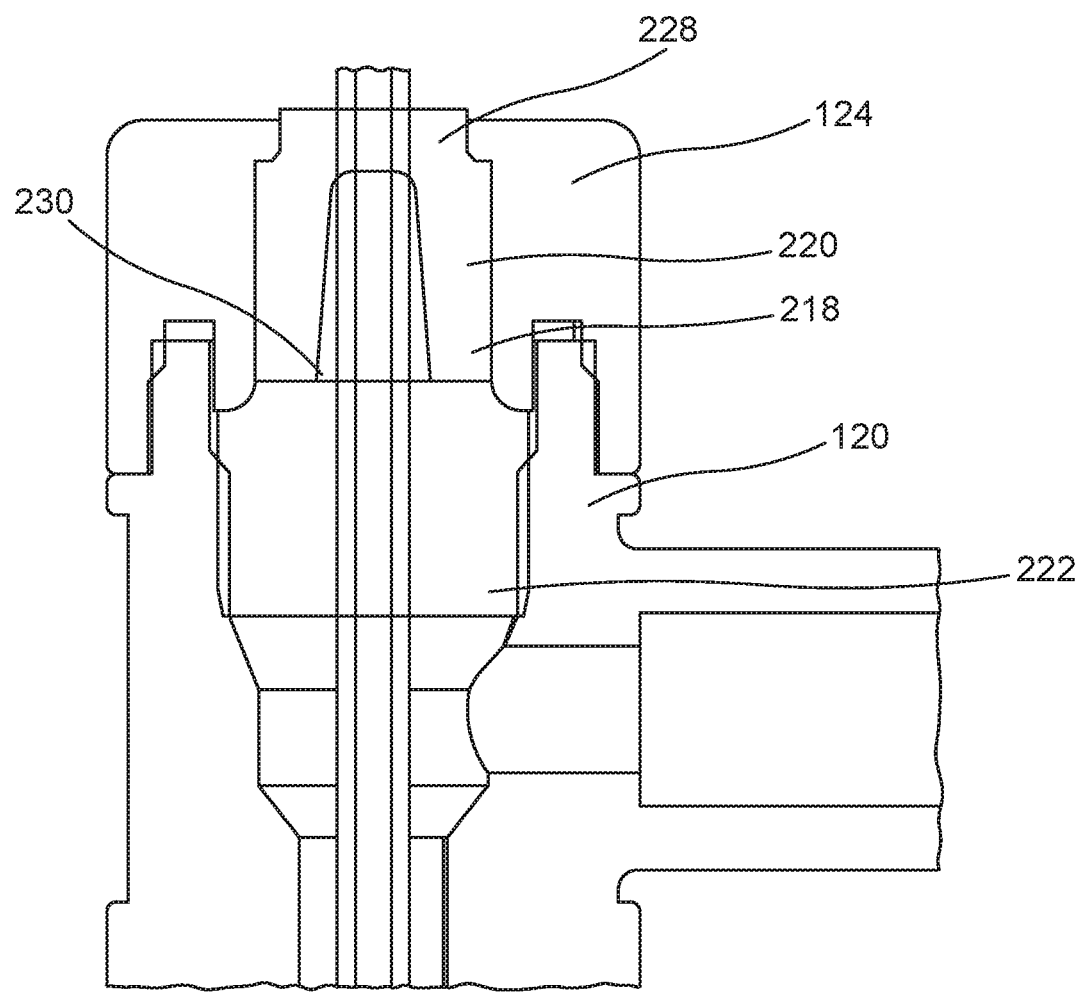
FIG. 13D illustrates a partial cross-sectional view of the second implementation of the valve within the catheter hub of the catheter group.

Referring to FIG. 13D, a partial cross-sectional view of the assembled rigid hub 120, two-part valve 218, and rigid hub cap 124 taken along the plane defined by the diameter of the rigid hub 120 and the longitudinal axis of the side port 121 is illustrated. The proximal region 228 having the reduced diameter is compressed within the rigid hub cap 124 to force the valve material radially inward in response to pressure applied to the flat distal face 226. The flat distal face 226 is flush with the distal end of the rigid hub cap 124 to allow for complete evacuation of the inner volume of the rigid hub 120 when flushing the catheter insertion device 100.

Figure 14:
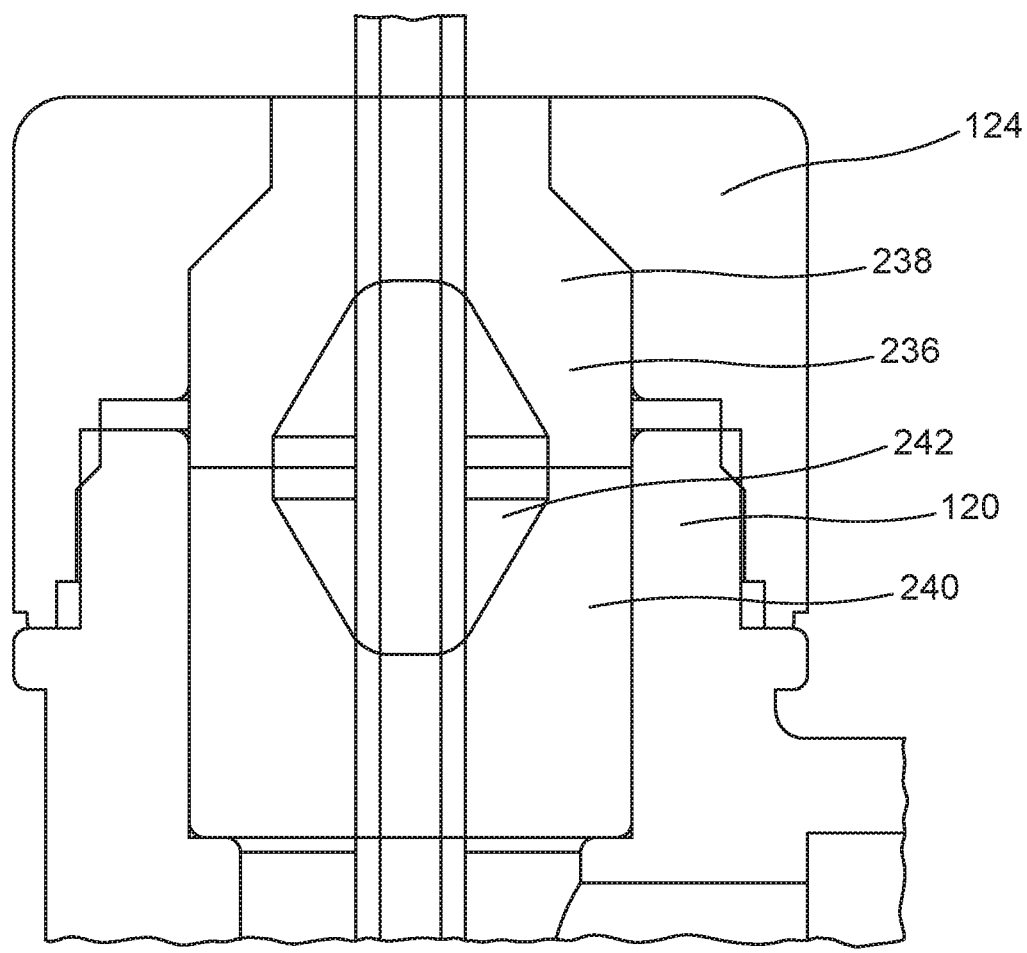
FIG. 14 illustrates a partial cross-sectional view of a third implementation of a valve within the catheter hub of the catheter group.

Referring to FIG. 14, a cross-sectional view of the assembled rigid hub 120, a third implementation of a two-part valve 236, and the rigid hub cap 124 taken along the plane defined by the diameter of the rigid hub 120 and the longitudinal axis of the side port 121 is illustrated. The valve 236 is a two-part valve that includes a proximal part 238 and a distal part 240. The proximal part 238 and the distal part 240 each define mirrored inner cavities that together define the inner cavity 242. As is the case with regard to the valve 218, the inner cavity 242 reduces the surface area of the valve 236 that the needle cannula 130 must pass through, thereby reducing the force required to insert the needle cannula 130. Based on the shape of the valve 236, the inner cavity of the proximal part 238 improves sealing when a vacuum is applied to the distal face of the distal part 240 following removal of the needle cannula 130. The inner cavity of the distal part 240 improves sealing when a high pressure is applied to the distal face of the distal part 240 following removal of the needle cannula 130. The valve 236 can be made of a resilient material, such as, for example, silicon, rubber, polyisoprene, or the like.

Figure 15:
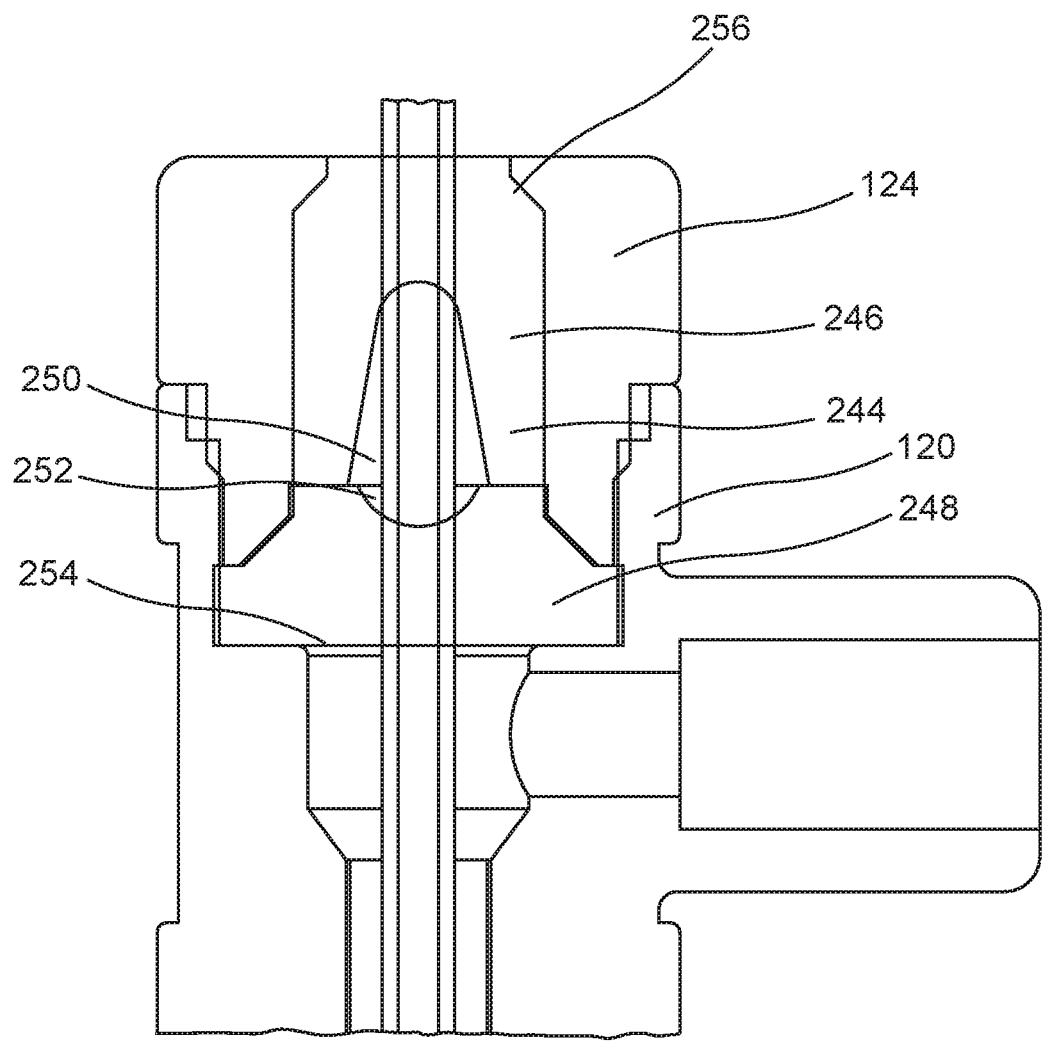
FIG. 15 illustrates a partial cross-sectional view of a fourth implementation of a valve within the catheter hub of the catheter group.

Referring to FIG. 15, a partial cross-sectional view of the assembled rigid hub 120, a fourth implementation of a two-part valve 244, and the rigid hub cap 124 taken along the plane defined by the diameter of the rigid hub 120 and the longitudinal axis of the side port 121 is illustrated. The valve 244 is a two-part valve that includes a proximal part 246 and a distal part 248. The proximal part 246 defines a proximal inner cavity 250 and the distal part 240 defines a relatively smaller distal inner cavity 252. Due to the compression provided by the rigid hub cap 124 on the proximal part 246 and the rigid hub 120 on the distal part 248, the valve 244 is sealed closed following removal of the needle cannula 130 from the valve 244.

Moreover, because of the distal inner cavity 252, the distal part 248 is forced radially inward to close the channel formed by the needle cannula 130 under pressure applied to the distal face 254 of the distal part 248. The pressure applied to the distal face 254 pushes the proximal part 246 proximally, which causes the wedged surface 256 of the valve 244 to compress within the rigid hub cap 124 and for the valve material radially inward.

In contrast, when a vacuum is applied to the distal face 254 of the distal part 248, the channel formed by the needle cannula 130 in the distal part 248 is forced open. The inner cavity of the proximal part 238, however, improves sealing when the vacuum is applied to the distal face 254 of the distal part 248 following removal of the needle cannula 130. In particular, the proximal part 246 is pulled distally which also causes the proximal part 246 to compress radially inward, thereby preventing air from entering the proximal inner cavity 250 from the outside environment. The valve 244 can be made of a resilient material, such as, for example, silicon, rubber, polyisoprene, or the like.

Figure 16:
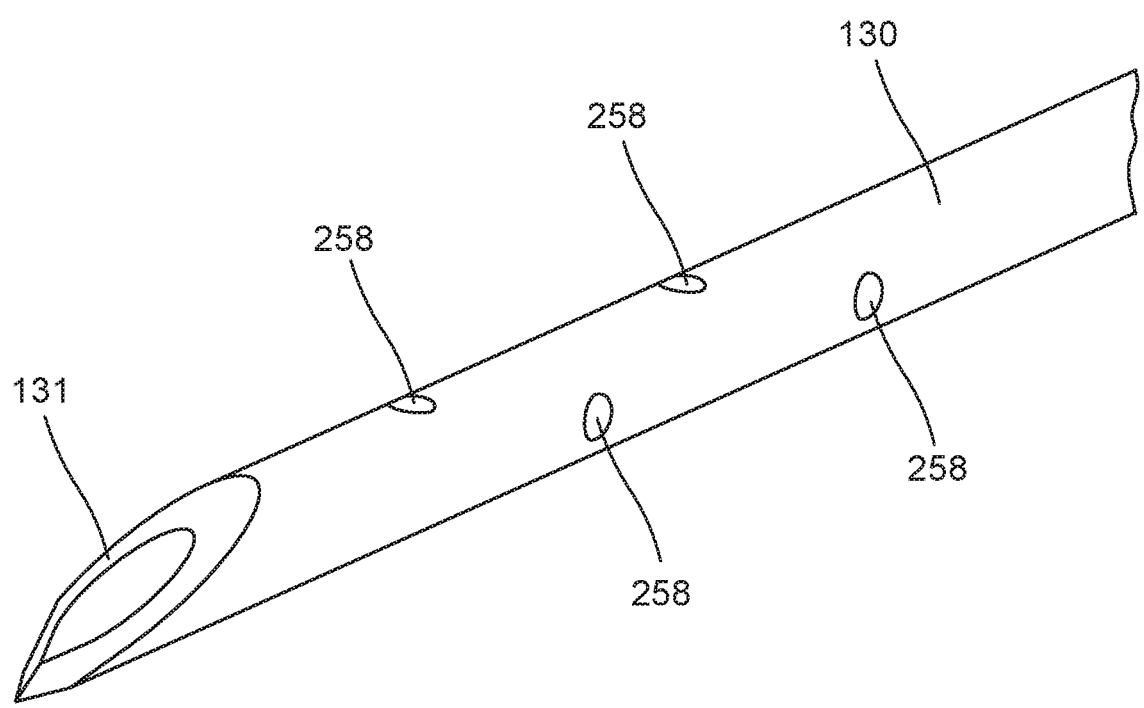
FIG. 16 illustrates a perspective view of a distal region of the needle showing a plurality of echogenic features.

Referring to FIG. 16, a perspective view of a distal region of the needle cannula 130 is illustrated. The distal region of the needle cannula 130 includes one or more and, preferably, eight echogenic features. The echogenic features can be, for example, through holes 258 drilled within opposite sides of the needle cannula 130. Although the sharp needle tip 131 is echogenic when observed under ultrasound, the through holes 258 improve the echogenicity of the needle cannula 130. In particular, the through holes 258 are visible through the wall thickness of the elongated catheter 106 under ultrasound. In addition, through holes 258 allow for blood flow from within the lumen of the needle cannula 130 to the outer surface of the needle cannula 130. The blood then flows to the inner surface of the catheter 106 to allow for visual observation of the blood.

The through holes 258 are angled relative to one another. For example, the through holes 258 are drilled 90 degrees apart from one another, as shown in FIG. 16. The different angles of the through holes 258 and the number of through holes 258 results in at least two echogenic features being visible under ultrasound at all times—one echogenic feature being the sharp needle tip 131 and the other being at least one of the through holes 258. The two visible echogenic features enable the practitioner to know the angle of insertion of the needle cannula 130.

Figure 17:
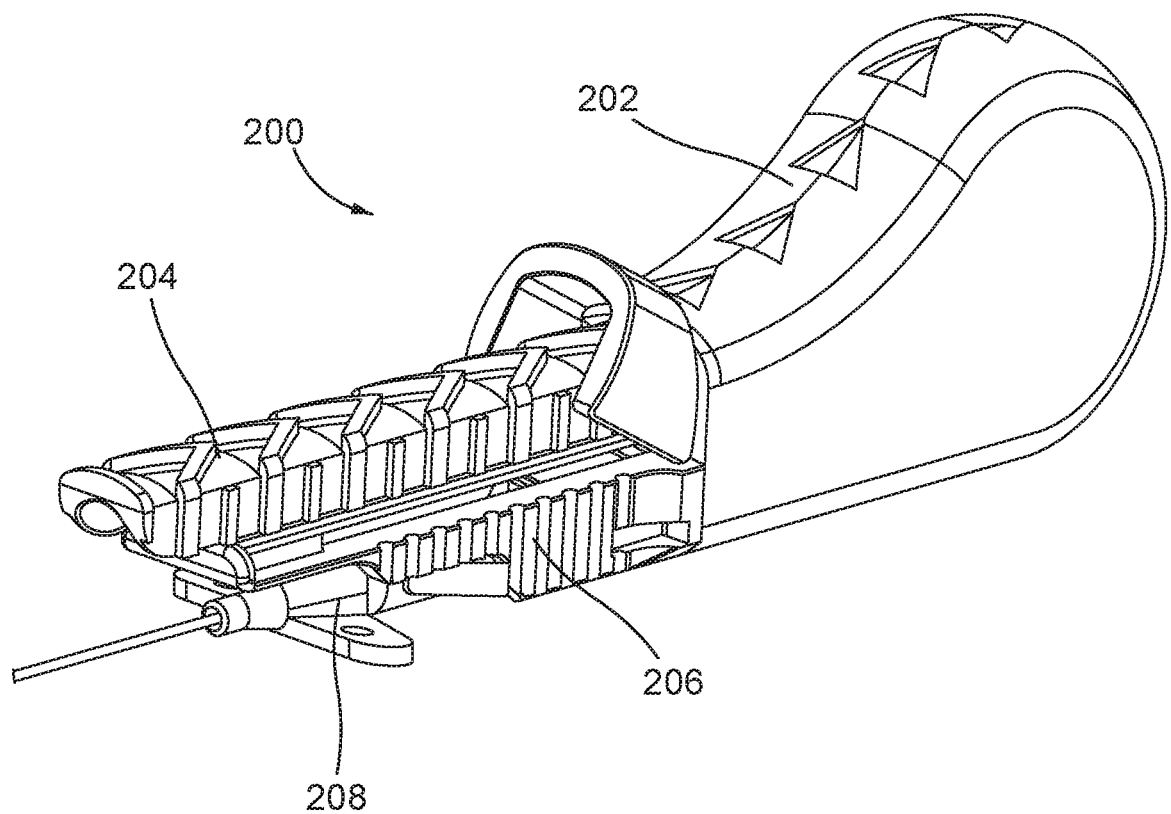
FIGS. 17-25 each illustrate an alternative implementation of catheter insertion device.

The many features and advantages of the catheter insertion device 100 are apparent from the detailed specification, and thus, the claims cover all such features and advantages within the scope of this application. Further, numerous modifications and variations are possible. For example, referring to FIGS. 17-25 various alternative implementations of catheter insertion devices are illustrated. In particular, the catheter insertion device 200 illustrated in FIG. 17 also includes a housing 202, a slider 204 that can be slid proximally to advance a guidewire distally and that can be slid distally to advance the guidewire proximally, and a release 206 to advance the catheter hub 208. Relative to the release 140 of the catheter insertion device 100, the release 206 is actuated below the slider 204.

Figure 18:
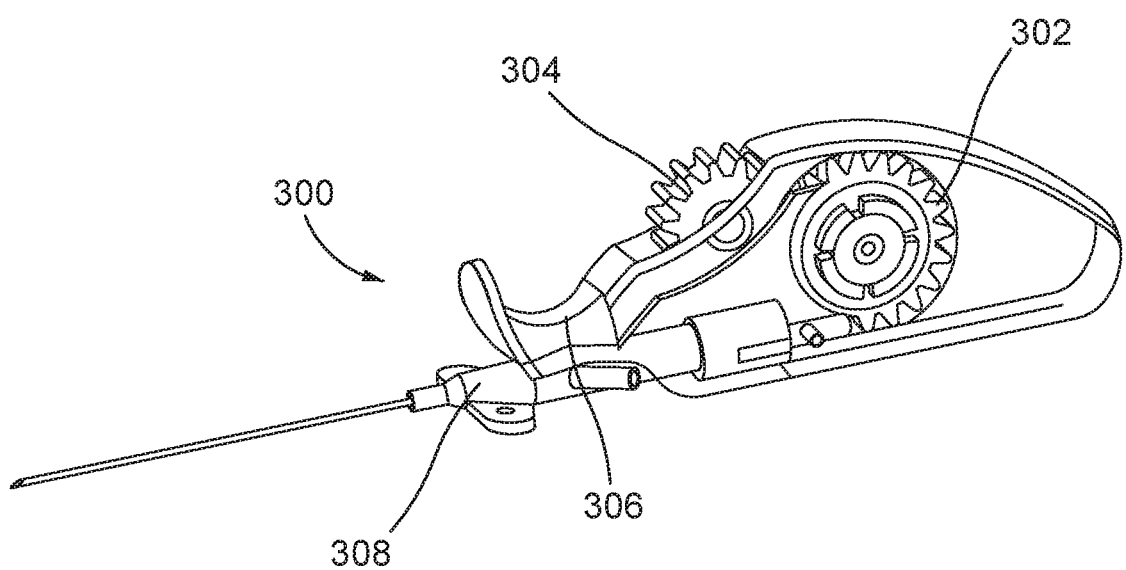

Referring to FIG. 18, the catheter insertion device 300 includes a housing 302, a wheeled actuator 304 that can be rotated counter clockwise to advance a guidewire distally and that can be rotated counter clockwise to advance the guidewire proximally, and a release 306 to advance the catheter hub 308. The wheeled actuator 304 limits the longitudinal movement of a finger of the practitioner to move the guidewire. In some implementations, the wheeled actuator 304 can be geared to further limit the movement of the practitioner to move the guidewire.

Figure 19:
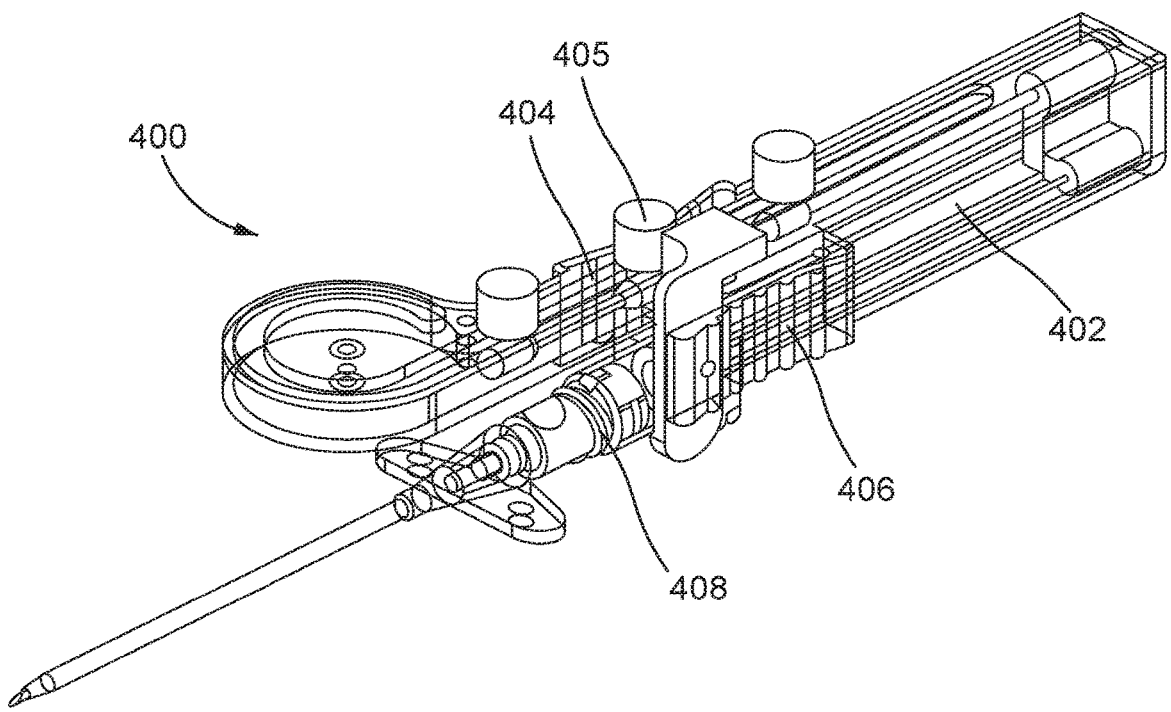

Referring to FIG. 19, the catheter insertion device 400 includes a housing 402, a linkage actuator 404 having links 405 that can be separately moved proximally to advance a guidewire distally and that can be moved distally to advance the guidewire proximally, and a release 406 to advance the catheter hub 408. The linkage actuator 404 enables the practitioner to control the length of advancement of the guidewire depending on the link 405 that is actuated.

Figure 20:
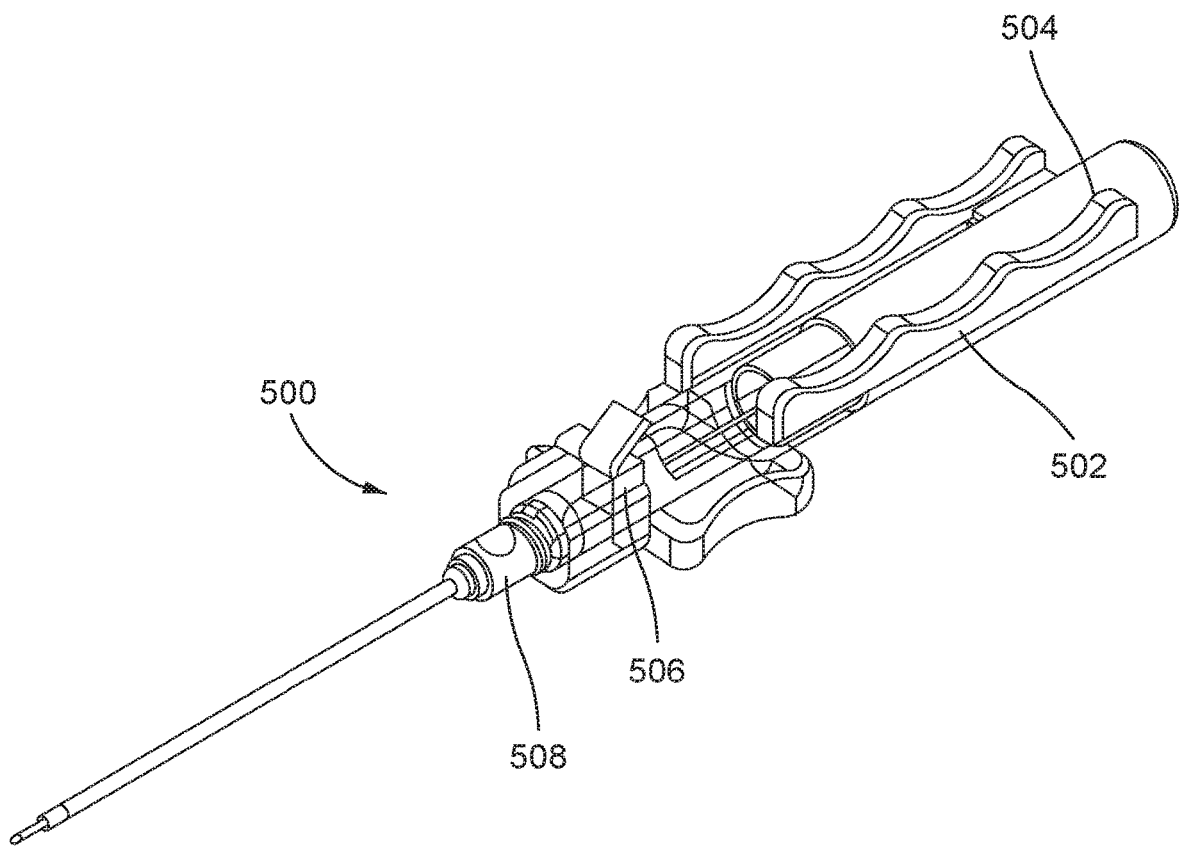

Referring to FIG. 20, the catheter insertion device 500 includes a housing 502 having grooves to receive the fingers of a practitioner, a piston 504 that is actuated to advance a guidewire distally, and a release 506 to disconnect the catheter hub 508. The piston 504 can be actuated by the thumb of the practitioner in a stepped manner.

Figure 21:
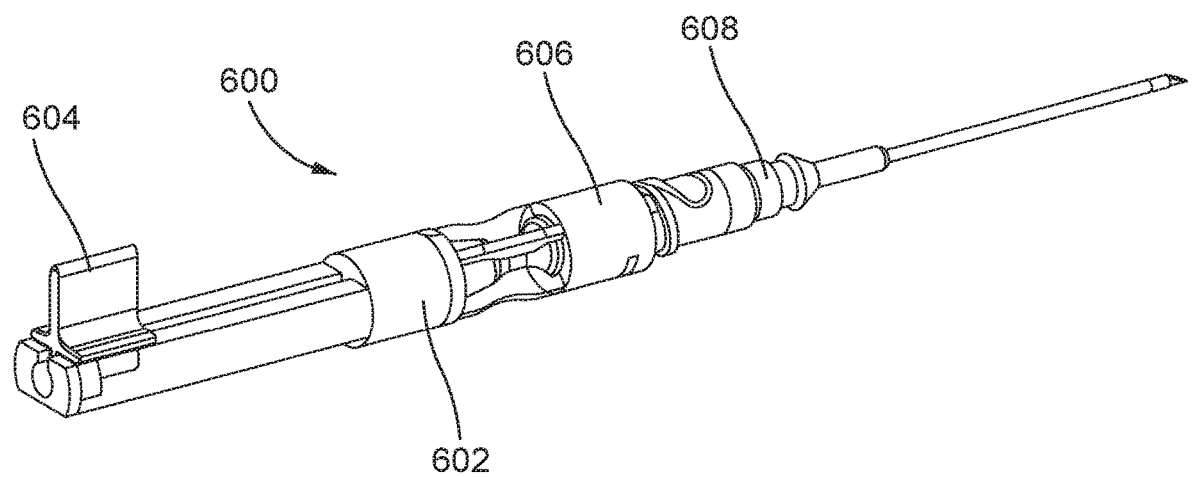

Referring to FIG. 21, the catheter insertion device 600 includes a housing 602, a single flag actuator 604 that is actuated to advance a guidewire distally or proximally, and a release 606 to disconnect the catheter hub 608. The release 606 is connected to the catheter hub 608 by a threaded connected and can be rotated relative to the catheter hub 608 to disconnect from the catheter hub 608. The single flag actuator 604 can be actuated by the thumb of the practitioner.

Figure 22:
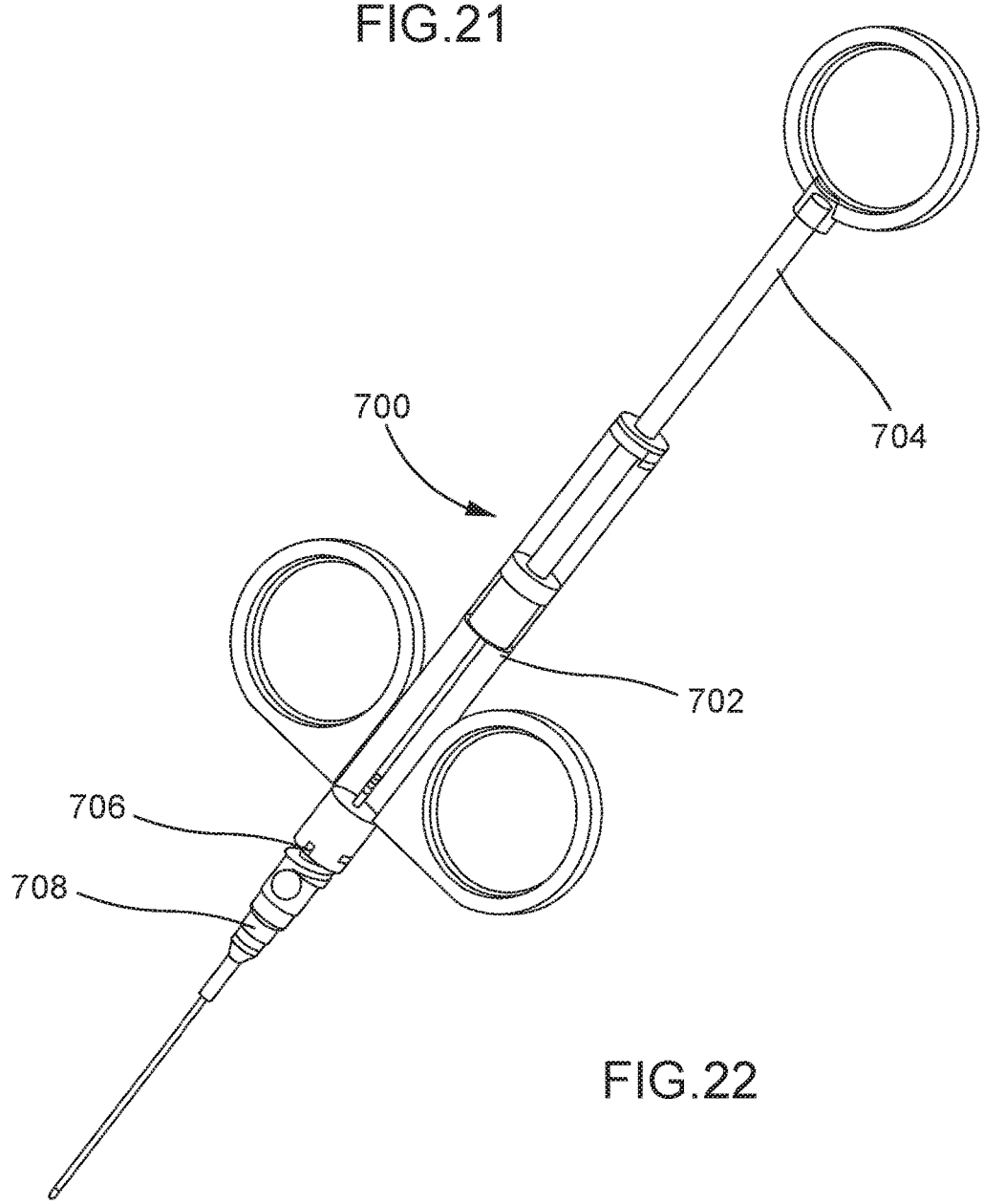

Referring to FIG. 22, the catheter insertion device 700 includes a housing 702, a plunger 704 that is actuated to advance a guidewire distally or proximally, and a release 706 to disconnect the catheter hub 708. The release 706 is connected to the catheter hub 708 through interference in the internal geometry of the catheter hub 708 and disconnects from the catheter hub 708 upon safety activation. The plunger 704 can be actuated by the thumb of the practitioner.

Figure 23:
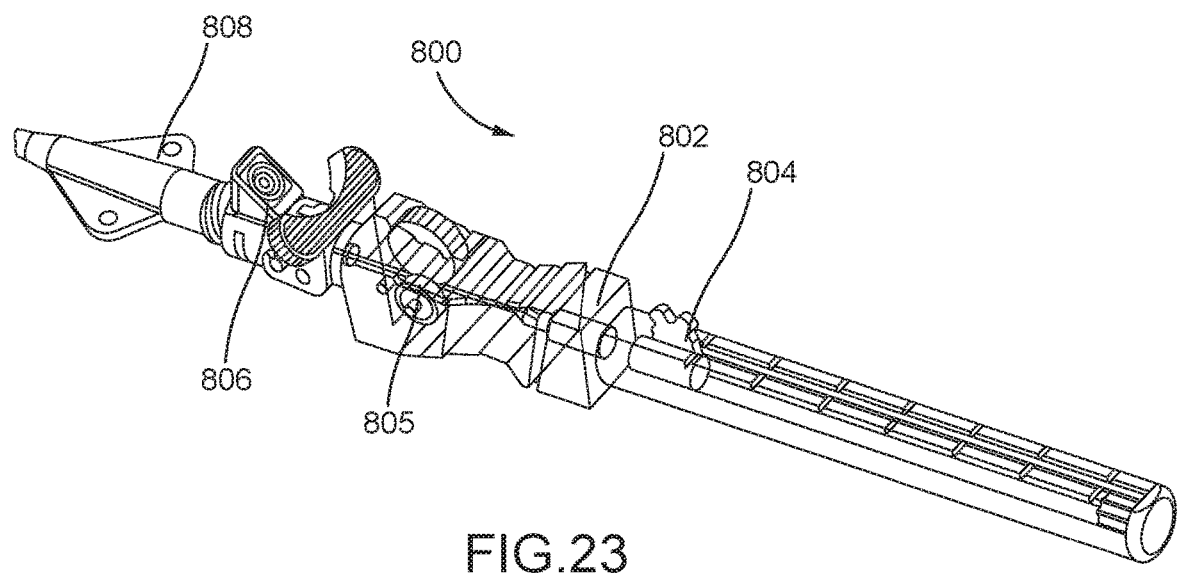
Figure 24:
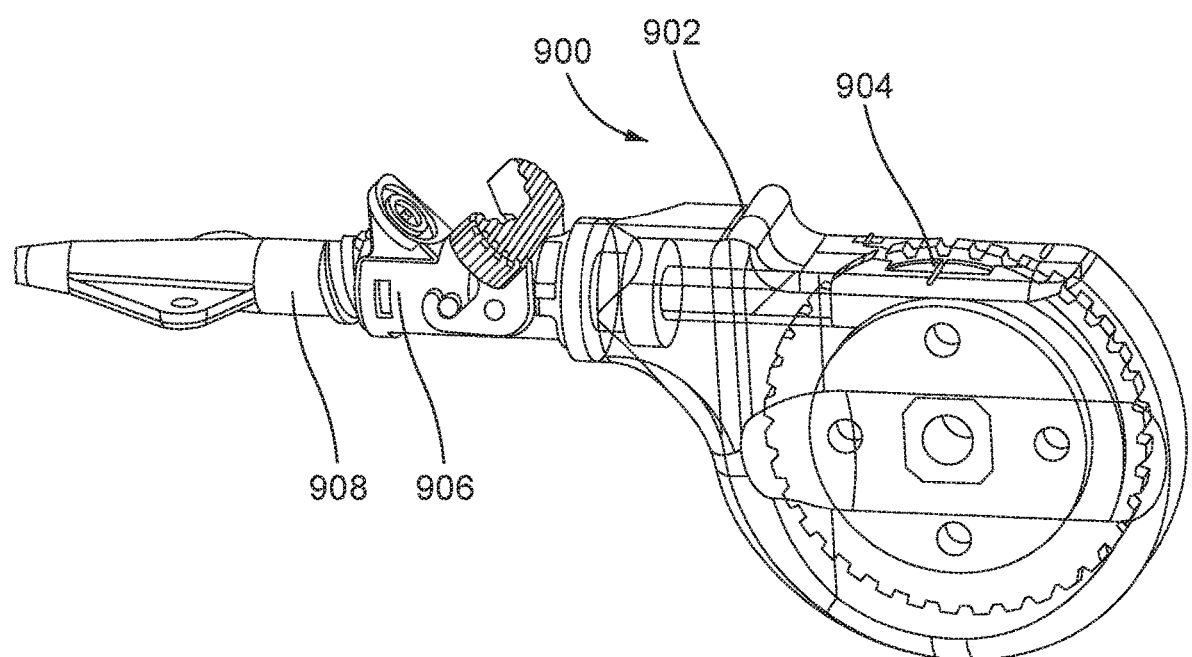

Referring to FIG. 23, the catheter insertion device 800 includes a housing 802, a single flag indicator 804 that is attached to the proximal end of a guide wire and shows the position of the guidewire distally or proximally to the tip of the needle, a partially exposed gearing mechanism 805 through which the guidewire passes, and a release 806 to disconnect the catheter hub 808. The gearing mechanism can be actuated by the finger of the practitioner to move the guidewire. Referring to FIG. 24, the catheter insertion device 900 includes a housing 902, a drum 904 that is directly actuated to advance a guidewire distally or proximally, and a release 906 to disconnect the catheter hub 908. The drum 904 can, for example, be rotated counter clockwise to advance a guidewire distally and that can be rotated counter clockwise to advance the guidewire proximally.

Figure 25:
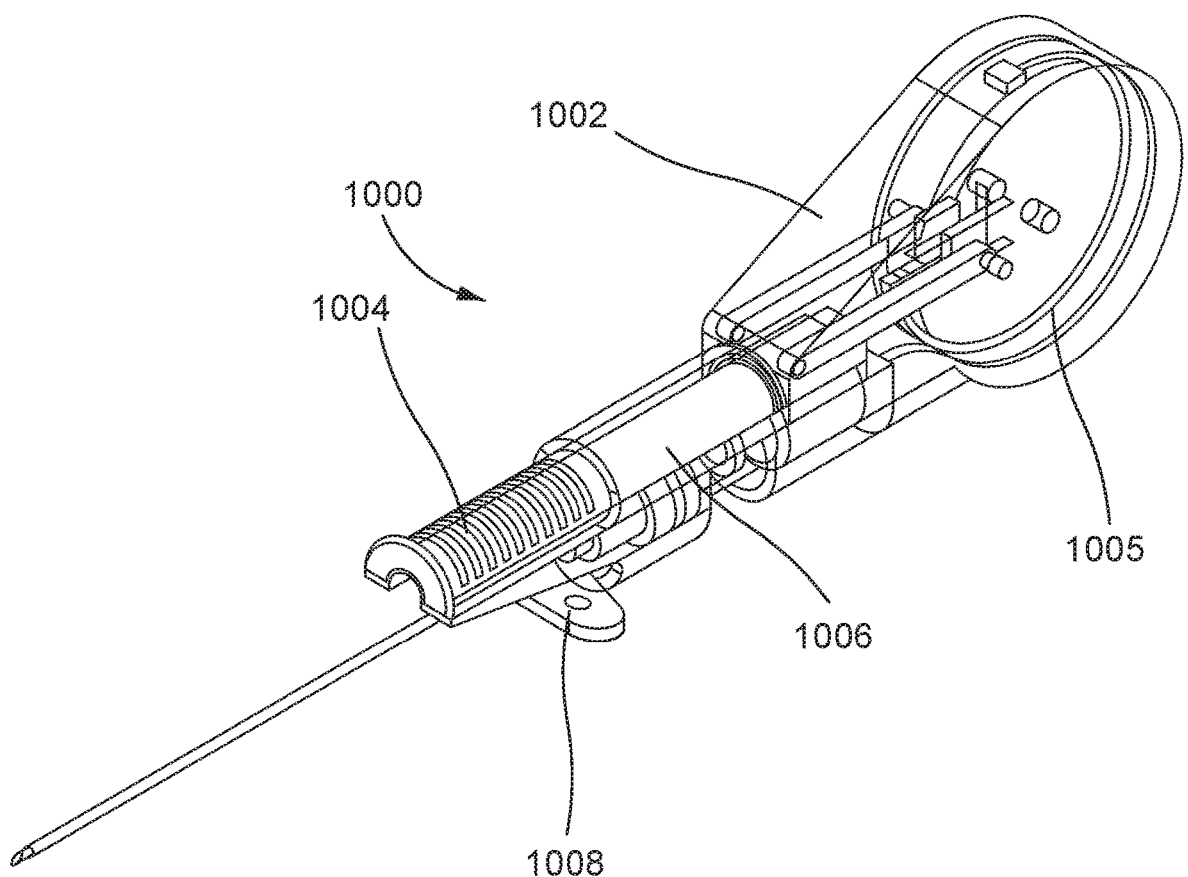

Referring to FIG. 25, the catheter insertion device 1000 includes a housing 1002, a slider 1004 that can be slid proximally to advance a guidewire distally and that can be slid distally to advance the guidewire proximally, a gearing mechanism or linkage configuration 1005 which can control the length of movement of the slider relative to the length of advancement of the guidewire, and a release 1006 to advance the catheter hub 1008.

As such, it is not desired to limit the catheter insertion device 100 to the exact construction and operation described and illustrated and, accordingly, all suitable modifications and equivalents may fall within the scope of the claims.

What is claimed is:

1. A catheter insertion device, comprising:
   an insertion group comprising a handle, a needle cannula partially within the handle, and a needle support connected to the handle; and
   a catheter group comprising an elongated catheter and a catheter hub connected to the proximal end of the elongated catheter, wherein:
   the needle support comprises two parallel features separated by a distance greater than an outer diameter of the elongated catheter to stabilize the needle cannula during insertion of the needle cannula into a patient, and
   the needle cannula having a cantilever portion extending from the handle, the needle support being configured to support the needle cannula on the cantilever portion, and wherein the needle support is configured to move relative to the handle by swinging relative to the handle.

2. The catheter insertion device of claim 1, wherein the needle support is configured to move relative to the handle upon abutment of the catheter hub to the needle support.

3. The catheter insertion device of claim 1, wherein the two parallel features are two parallel walls.

4. The catheter insertion device of claim 1, wherein the handle comprises a top arm, and the needle support is connected to a distal region of the top arm of the handle.

5. The catheter insertion device of claim 1, wherein the needle support is configured to stabilize an intermediate portion of the needle cannula during insertion of the needle cannula into a patient, said intermediate portion of the needle cannula freely extending from the handle.

6. The catheter insertion device of claim 1, further comprising a guidewire partially within the handle and the needle cannula.

7. The catheter insertion device of claim 6, further comprising a first actuator connected to the handle and the guidewire, the first actuator being movable relative to the handle to move the guidewire relative to the handle.

8. The catheter insertion device of claim 7, wherein the first actuator comprises an arm extending downward from a bottom surface of the first actuator, the arm being connected to a proximal end of the guidewire.

9. The catheter insertion device of claim 7, wherein the first actuator is a slider operable to slide over a portion of the handle.

10. The catheter insertion device of claim 7, wherein the needle support comprises a top portion that abuts a bottom surface of the first actuator to prevent movement of the needle support relative to the handle.

11. The catheter insertion device of claim 7, further comprising a second actuator connected to the handle, the second actuator being movable relative to the handle to push the catheter group relative to the handle.

12. The catheter insertion device of claim 11, wherein the second actuator comprises a notch configured to receive a portion of the catheter hub.

13. The catheter insertion device of claim 11, wherein the second actuator comprises an enlarged proximal end that engages with the handle to limit travel of the second actuator relative to the handle.

14. A method of using a catheter insertion device, the method comprising:
  receiving, by a practitioner, the catheter insertion device, the catheter insertion device comprising:
    a handle,
    a needle cannula partially within the handle, the needle cannula comprising a sharp distal tip extending distally from the handle,
    a guidewire partially within the handle and the needle cannula,
    a first actuator connected to the handle and the guidewire, the first actuator being movable relative to the handle to move the guidewire relative to the handle,
    a catheter group removably connected to the handle, the catheter group comprising an elongated catheter and a catheter hub connected to the proximal end of the elongated catheter, and
    a second actuator connected to the handle, the second actuator being movable relative to the handle to move the catheter group relative to the handle;
  gripping the handle using a hand of the practitioner;
  navigating the handle until the sharp distal tip of the needle cannula is within the vasculature of a patient;
  actuating the first actuator using a first finger of the hand of the practitioner to cause a distal tip of the guidewire to move in a distal direction relative to the handle and within the vasculature of the patient; and
  actuating the second actuator using the first finger of the practitioner to cause the catheter group to move in a distal direction relative to the handle so that the distal end of the elongated catheter is inserted within the vasculature of the patient.

15. The method of using the catheter insertion device of claim 14, wherein the handle comprises a first side and a second side opposite the first side, the method further comprising:
  gripping the first side using a second finger of a hand of the practitioner; and
  gripping the second side using a third finger of the hand of the practitioner, the second finger and the third finger being different from the first finger used to actuate the first actuator and the second actuator.

16. The method of using the catheter insertion device of claim 14, wherein:
  the first actuator is actuated in a proximal direction using the first finger of the hand of the practitioner to cause a distal tip of the guidewire to move in a distal direction relative to the handle and within the vasculature of the patient; and
  the second actuator is actuated in a distal direction using the first finger of the practitioner to cause the catheter group to move in a distal direction relative to the handle so that the distal end of the elongated catheter is inserted within the vasculature of the patient.

17. The method of using the catheter insertion device of claim 14, further comprising gripping the catheter hub with the other hand of the practitioner while pulling the handle in a proximal direction using the hand of the practitioner to separate the catheter group from the handle.

18. The method of using the catheter insertion device of claim 14, wherein the practitioner grips the handle overhand, and the first finger is the index finger of the hand of the practitioner.

19. The method of using the catheter insertion device of claim 14, wherein the practitioner grips the handle underhand, and the first finger is the index finger of the hand of the practitioner.

* * * * *